(12) United States Patent
Donovan et al.

(10) Patent No.: US 8,980,614 B2
(45) Date of Patent: Mar. 17, 2015

(54) STAPHYLOCOCCUS HAEMOLYTICUS PROPHAGE φSH2 ENDOLYSIN IS LYTIC FOR STAPHYLOCOCCUS AUREUS

(75) Inventors: David M. Donovan, Baltimore, MD (US); Igor V. Abaev, Obolensk Moscow Region (RU); Mathias Schmelcher, Gockhausen (CH)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 81 days.

(21) Appl. No.: 13/605,200

(22) Filed: Sep. 6, 2012

(65) Prior Publication Data

US 2014/0065127 A1  Mar. 6, 2014

(51) Int. Cl.
*C12N 1/20* (2006.01)
*C12N 9/26* (2006.01)
*C12N 15/00* (2006.01)
*C12N 9/24* (2006.01)
*C12N 9/36* (2006.01)

(52) U.S. Cl.
CPC ....... *C12N 9/2402* (2013.01); *C12Y 302/01017* (2013.01); *C12N 9/2462* (2013.01)
USPC .............. 435/252.3; 435/201; 435/320.1; 536/23.2

(58) Field of Classification Search
CPC ....................................... C12N 9/2402
USPC ............................................ 453/201
See application file for complete search history.

(56) References Cited

U.S. PATENT DOCUMENTS 8,232,370 B2 * 7/2012 Yoon et al. .............. 530/350
2010/0158886 A1 * 6/2010 Donovan et al. ......... 424/94.3

* cited by examiner

*Primary Examiner* — Tekchand Saidha
(74) *Attorney, Agent, or Firm* — John D. Fado; Evelyn M. Rabin

(57) ABSTRACT

Methicillin-resistant (MRSA) and multi-drug resistant strains of *Staphylococcus aureus* are becoming increasingly prevalent in both human and veterinary clinics. *S. aureus*-causing bovine mastitis yields high annual losses to the dairy industry. Treatment of mastitis by broad range antibiotics is often not successful and may contribute to development of antibiotic resistance. Bacteriophage endolysins are a promising new source of antimicrobials. The endolysin of prophage φSH2 of *Staphylococcus haemolyticus* strain JCSC1435 (φSH2 lysin) shows lytic activity against live staphylococcal cells. Deletion constructs were tested in zymograms and turbidity reduction assays to evaluate the contribution of each functional module to lysis. The CHAP domain exhibited three-fold higher activity than the full length protein. Activity was further enhanced in the presence of bivalent calcium ions. The full length enzyme and the CHAP domain showed activity against multiple staphylococcal strains, including MRSA strains, mastitis isolates, and coagulase negative staphylococcal (CoNS) strains.

9 Claims, 5 Drawing Sheets
(1 of 5 Drawing Sheet(s) Filed in Color)

|    | Construct | Purification | Activity |
|----|-----------|--------------|----------|
|    | 1-493 (CHAP 38-162, Amidase 204-339, SH3b 410-475, 6His 493) | + | + |
| A1 | 1-166 (NdeI/XhoI) | + | +++ |
| A2 | 1-210 (NdeI/XhoI) | + | - |
| A3 | 1-245 (NdeI/XhoI) | (+) | - |
| A4 | 1-287 (NdeI/XhoI) | - | n.d. |
| B1 | 1-166 | 341-493 (NdeI/XhoI/XhoI) | (+) | - |
| B2 | 1-245 | 347-493 (NdeI/XhoI/XhoI) | - | n.d. |
| C1 | 1-397 (NdeI/XhoI) | + | (+) |
| C2 | 1-429 (NdeI/XhoI) | - | n.d. |
| D1 | 178-397 (NdeI/XhoI) | + | - |
| D2 | 178-429 (NdeI/XhoI) | (+) | - |
| E1 | 178-493 (NdeI/XhoI) | + | (+) |
| E2 | 148-493 (NdeI/XhoI) | (+) | - |

Fig. 1

STAPHYLOCOCCUS HAEMOLYTICUS PROPHAGE φSH2 ENDOLYSIN IS LYTIC FOR STAPHYLOCOCCUS AUREUS

BACKGROUND OF THE INVENTION

1. Field of the Invention

This invention relates to a nucleic acid sequence encoding a functional module or domain of a particular peptidoglycan hydrolase, i.e., the φSH2 prophage endolysin, a protein which specifically attacks the cell wall peptidoglycan of untreated *Staphylococcus aureus* and coagulase negative staphylococci (*S. chronogenes, S. epidermis, S. hyicus, S. simulans, S. warneri*, and *S. xylocus*). The φSH2 prophage endolysin is active over a broad range of physiological conditions including the pH and calcium concentration of bovine milk. The invention further relates to methods of treating diseases caused by the bacteria for which the φSH2 prophage endolysin is specific.

2. Description of the Relevant Art

*Staphylococcus* is a genus of Gram-positive cocci that includes both human and animal pathogens. Multiple drug resistant strains of *S. aureus* (e.g., methicillin-resistant *S. aureus*, MRSA) pose a major threat to human health. A recent study reports clinical estimates indicating that MRSA strains caused more than 94,000 serious infections and more than 18,000 deaths in the United States in 2005 (Klevens et al. 2007. *JAMA* 298:1763-1771).

Also in the dairy industry, staphylococci are a persistent problem. Bovine mastitis, an infection of the mammary gland, results in annual losses between $1.7 billion and $2 billion in the United States alone (Sordillo et al. 2002. *J. Mammary Gland Biol. Neoplasia* 7 (2): 135-146). *S. aureus* is among the most relevant causative agents of this disease, accounting for 18% of mastitis cases in a study carried out on dairy herds in the states of New York and Pennsylvania (Wilson et al. 1997. *J. Dairy Sci.* 80: 2592-2598). The conventional method of treatment by antibiotics is often less than 50% effective and often leads to premature culling (Deluyker et al. 2005. *J. Dairy Sci.* 88:604-614). Furthermore, the use of broad range antibiotics such as pirlimycin and penicillin, which are commonly applied for treatment of mastitis (Cattell et al. 2001. *J. Dairy Sci.* 84:2036-2043), can contribute to the development of resistance in mastitis pathogens and nonrelated bacteria (Fischetti, V. A. 2005. *Trends Microbiol.* 13:491-496; Lee, J. H. 2003. *Appl. Environ. Microbiol.* 69:6489-6494; Vanderhaeghen et al. 2010. *Epidemiol. Infect.* 138:606-625). In an international study including several European countries and the United States, 57% of 811 *S. aureus* isolates from bovine mastitis were shown to be β-lactamase positive (De Oliveira et al. 2000. *J. Dairy Sci.* 83(4): 855-862). Moreover, there is a debate on whether antibiotic resistance can be transferred from farm animals to humans (Ferber, D. 2002. *Science* 295:27-28; Ferber, D. 2003. *Science* 301:1027).

In contrast to antibiotics, the use of pathogen-specific antimicrobials such as bacteriophage endolysins is expected to reduce the risk of resistance development (Walsh, C. 2003. *Nat. Rev. Microbiol.* 1:65-70). Bacteriophage endolysins are proteins which are produced inside an infected host cell at the end of the lytic multiplication cycle of the phage in order to lyse the bacterial cell from within, thereby releasing the phage progeny. In most cases, the lysis event is triggered by the action of a holin, another phage encoded protein which creates pores in the cytoplasmic membrane, enabling the endolysin to gain access to the host cell wall and degrade the peptidoglycan (Young and Blasi. 1995. *FEMS Microbiol. Rev.* 17:191-205). When exposed externally to Gram positive bacteria, in the absence of an outer membrane, these enzymes can also degrade the peptidoglycan, and lyse the cells. This makes them potential antimicrobials against Gram-positive pathogens such as *Staphylococcus aureus* (Fischetti, supra; Loessner et al. 2005. *Curr. Opin. Microbiol.* 8: 480-487). Furthermore, development of resistance in Gram-positive organisms against the highly specific action of phage endolysins is believed unlikely due to coevolution of phage and host, and up to now no resistant strains have been reported despite repeated efforts to find them (Fischetti, supra; Loeffler et al. 2001. *Science* 294:2170-2172; Schuch et al. 2002. *Nature* 418:884-889). Bacterial strains resistant against other (non-endolysin) peptidoglycan hydrolases such as the bacteriocin Lysostaphin (Dehart et al. 1995; Gründling et al. 2006. *J. Bacteriol.* 188:6286-6297; Sugai et al 1997. *J. Bacteriol.* 179: 4311-4318) or human lysozyme (Guariglia-Oropeza and Helmann. 2011. *J. Bacteriol.* 193:6223-6232; Vollmer, W. 2008. *FEMS Microbiol. Rev.* 32:287-306) have been described. Resistance against Lysostaphin has been ascribed in most cases to changes within the pentaglycine bridge (Dehart et al., supra; Rohrer et al. 1999. *Proc. Natl. Acad. Sci. USA* 96:9351-9356; Stranden et al. 1997. *J. Bacteriol.* 179: 9-16; Sugai et al., supra; Thumm and Götz. 1997. *Mol. Microbiol.* 23:1251-1265), which is the target of Lysostaphin (Schindler and Schuhardt. 1964. *Proc. Natl. Acad. Sci. USA* 51:414-421) and presumably constitutes the most variable part of staphylococcal peptidoglycan (Schleifer and Kandler. 1972. *Bacteriol. Rev.* 36:407-477).

Endolysins from a Gram-positive background show a modular architecture, consisting of one or more enzymatically active domains, which cleave certain bonds within the bacterial peptidoglycan, and often a cell wall binding domain, which directs the enzyme to its substrate and confers specificity for the target cells. The latter is usually located at the C-terminus of the protein (Borysowski et al. 2006. *Exp. Biol. Med. (Maywood)* 231:366-377; Fischetti, supra; Loessner 2005, supra). According to the bonds cleaved by the enzymatically active domains, these domains can be classified into five different groups: (i) muramidases (also known as lysozymes) and (ii) glucosaminidases, which are both glycosidases and cleave the N-acetylmuramoyl-β-1,4-N-acetylglucosamine and N-acetylglucosaminyl-β-1,4-N-acetylmuramine bonds within the glycan strand of the peptidoglycan, respectively; (iii) lytic transglycosylases, which cleave the same bond as muramidases, but by a different mechanism; (iv) amidases, which cut between the glycan and the peptide moieties; and (v) endopeptidases, which cleave within the peptide moiety. The latter can be further divided into those enzymes cutting within the stem peptide, those cutting within the inter-peptide bridge, and those cleaving between the stem peptide and the inter-peptide bridge (Borysowski et al., supra; Hermoso et al. 2007. *Curr. Opin. Microbiol.* 10: 461-472; Loessner, M. J., supra). As demonstrated by several studies, the modular organization of phage endolysins allows artificial rearrangement of their functional domains, yielding protein chimeras with new and potentially optimized properties for control of pathogens (Becker et al. 2009b. *Gene* 443, 32-41; Croux et al. 1993a. *Mol. Microbiol.* 9:1019-1025; Croux et al. 1993b. *FEBS Lett.* 336:111-114; Diaz et al. 1990. *Proc. Natl. Acad. Sci. U.S.A.* 87:8125-8129; Donovan et al. 2006a. *Appl. Environ. Microbiol.* 72:2988-2996; Schmelcher et al. 2011. *Microb. Biotechnol.* 4:651-662). Therefore, bacteriophage endolysins do not only represent a promising alternative to antibiotics in their native form, but also a source of functional modules for the construction of tailor-made antimicrobials (Donovan et al. 2009. *Biotech International* 21:6-10).

The genomic sequence of *Staphylococcus haemolyticus* strain JCSC1435 was published recently, and two prophages were identified within the genome (Takeuchi et al. 2005. *J. Bacteriol.* 187:7292-7308). One of the prophages, φSH2, contains a gene (SH2333) coding for a putative endolysin, which was annotated as N-acetylmuramoyl-L-alanine amidase (BAE05642.1). Bioinformatic analysis suggests that this protein consists of two enzymatically active domains and one C-terminal cell wall binding domain. A conserved domain database (retrieved from the Internet: <URL: ncbi.nlm.nhi.gov) search identified a CHAP (Cysteine, Histidine-dependent Amidohydrolases/Peptidases) domain (pfam#PF05257; Bateman and Rawlings. 2003. *EMBO J.* 15:4789-4797; Rigden et al. 2003. *Trends Biochem. Sci.* 28:230-234) at the N-terminus, an Amidase_2 domain (N-acetylmuramoyl-L-alanine amidase; pfam#PF01510) in the center, and a bacterial SH3 domain (SH3b domain), which is associated with cell wall binding, at the C-terminus of the protein (pfam#PF08460; Whisstock and Lesk. 1999. *Trends Biochem. Sci.* 24:132-133). The crystal structure of one representative of the Amidase_2 family, the AmiE domain of the major *S. epidermidis* autolysin AtlE has recently been reported as the first protein structure with an amidase-like fold from a Gram-positive bacterial background, and also the structure of its binding domain and the phylogenetic relationship of the protein have been analyzed (Albrecht et al. 2012. *J. Bacteriol.* 194:2630-2636; Zoll et al. 2010. PLoS Pthog. 6: e1000807; Zoll et al. 2012. *J. Bacteriol.* 194:3789-3802). The φSH2 lysin shares its domain architecture with a number of other staphylococcal lysins described so far, such as the φ11 prophage endolysin LytA (Wang et al. 1991. *Gene* 102:105-109), the phage K endolysin LysK (O'Flaherty et al. 2005. *J. Bacteriol.* 187:7161-7164), the phage Twort endolysin plyTW (Loessner et al. 1998. *FEMS Microbiol. Lett.* 162: 265-274), and the *S. warneri* phage WMY endolysin lysWMY (Yokoi et al. 2005. *Gene* 351:97-108). When more than fifty SH3b-containing staphylococcal peptidoglycan hydrolases (including the aforementioned phage endolysins) were classified based on overall sequence homology, the majority of the proteins fell into five groups featuring mostly >90% within-group but mostly <50% between-group sequence identity. The φSH2 lysin (previously referred to as "haemolyticus JCSC1435") was one of six "stand-alone" proteins that shared less than 50% identity with any of the groups (Becker et al. 2009b, supra).

Peptidoglycan structure varies only slightly between different species and strains of the genus *Staphylococcus*, comprising a highly conserved stem peptide and a glycine-rich inter-peptide bridge (usually a penta- or hexa-glycine bridge) in which single residues can be replaced by L-serine or L-alanine (Schleifer and Kandler, supra). Therefore, it is not uncommon that an endolysin from a phage specific for a certain staphylococcal species also shows activity against other species of the genus, as demonstrated for lysWMY (Yokoi et al., supra) and LysK (Becker et al. 2009a. *FEMS Microbiol. Lett.* 294:52-60). *S. haemolyticus* peptidoglycan differs from that of *S. aureus* (pentaglycine bridge) by variations of the inter-peptide bridge, the most predominant cross bridges being COOH-Gly-Gly-Ser-Gly-Gly-NH$_2$ and COOH-Ala-Gly-Ser-Gly-Gly-NH2 (Billot-Klein et al. 1996. *J. Bacteriol.* 178:4696-4703).

To counter the rise of drug resistant pathogenic bacteria, there is a need for new specific antimicrobial treatments. Reagents shown to be very specific for the genera, species or strains of concern would give better effective control of economically important diseases and therefore are ideal candidates for therapeutic treatments.

SUMMARY OF THE INVENTION

We have discovered that the nucleic acid encoding φSH2 prophage endolysin, a protein which specifically attacks the peptidoglycan cell wall of untreated *S. aureus* and coagulase negative staphylococci can be truncated and that φSH2 prophage endolysin, and also truncations of φSH2 prophage endolysin, can be used as an antimicrobial treatment for mastitis as well as for infection and for other human diseases, such as infection and disease caused by multidrug-resistant staphylococci.

In accordance with this discovery, it is an object of the invention to provide nucleic acid molecules encoding φSH2 endolysin or truncated φSH2 endolysin polypeptides.

It is also an object of the invention to provide an antimicrobial φSH2 endolysin or a truncated φSH2 endolysin, which is functional, i.e., retains its properties for degrading the peptidoglycan cell wall of the Gram-positive bacteria.

An added object of the invention is to provide a nucleic acid sequence encoding φSH2 endolysin or truncated φSH2 endolysin polypeptides according to the invention as an encoding sequence which allows disease resistance to be imparted to the organism. It is well understood that this sequence can also be used in combination with another sequence, or sequences, encoding one or more disease resistant properties.

It is an object of the invention to provide a nucleic acid sequence encoding φSH2 endolysin or truncated φSH2 endolysin polypeptides according to the invention as an encoding sequence which can be expressed in the mammary glands of transgenic cattle.

It is a further object of the invention to provide a nucleic acid encoding an antimicrobial fusion protein formed from a nucleic acid encoding a functional module or domain of the φSH2 endolysin, a protein which specifically attacks the peptidoglycan cell wall of untreated *S. aureus* and coagulase negative staphylococci in combination with nucleic acid encoding a functional module(s) or domain(s) of another endolysin(s) having a different hydrolase activity, e.g., glycosidase, amidase and endopeptidase activity.

A still further object of the invention also relates to a chimeric gene (or expression cassette) comprising an encoding sequence as well as heterologous regulatory elements in positions 5' and 3' which can function in a host organism, the encoding sequence comprising at least one nucleic acid sequence encoding an antimicrobial φSH2 endolysin or a truncated φSH2 endolysin.

An additional object of the invention is to provide a host organism into which the φSH2 gene, or truncated gene, according to the invention can be introduced so as to produce an endolysin or truncated endolysin.

An added object of the invention is to provide compositions comprising an antimicrobial φSH2 endolysin or a truncated φSH2 endolysin, compositions useful for the treatment of disease caused by the bacteria for which the φSH2 endolysin and truncated φSH2 endolysin are specific.

Also part of this invention is a kit, comprising a composition for treatment of disease caused by the bacteria for which the φSH2 endolysin and truncated φSH2 endolysin are specific.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIG. 1 depicts a schematic representation of the full length φSH2 lysin and deletion constructs. The full length C-terminally 6×His-tagged protein (top) and all truncation constructs of the enzyme created in this work are shown. The nucleic acid molecules encoding the full length φSH2 lysin (SEQ ID NO:1) and deletion constructs: pφSH2_A1 (SEQ ID NO:3), pφSH2_A2 (SEQ ID NO:5), pφSH2_A3 (SEQ ID NO:7), pφSH2_A4 (SEQ ID NO:9), pφSH2_B1 (SEQ ID NO:11), pφSH2_B2 (SEQ ID NO:13), pφSH2_C1 (SEQ ID NO:15), pφSH2_C2 (SEQ ID NO:17), pφSH2_D1 (SEQ ID NO:19), pφSH2_D2 (SEQ ID NO:21), pφSH2_E1 (SEQ ID NO:23), and pφSH2_E2 (SEQ ID NO:25) comprise nucleotides encoding C-terminal LE,HHHHHH residues. The full length and truncated proteins encoded by these nucleic acid sequences are identified by SEQ ID NOs: 2, 4, 6, 8, 10, 12, 14, 16, 18, 20, 22, 24, and 26, respectively. Amino acid positions of functional domains (in the full length protein) and restriction sites used for cloning of fragments (in the deletion constructs) are indicated. The number of amino acids of the full length protein (493 AA) excludes the C-terminal 6×His-tag. In the 'Purification' column, all constructs that could be purified at a concentration of >0.5 mg/ml and an estimated purity of >90% under native conditions are rated with '+'; '(+)' marks constructs that yielded lower concentrations and/or purities when purified under native conditions; and '−' indicates constructs for which no soluble protein could be obtained under native conditions. In the 'Activity' column, lytic activity of all constructs as determined by turbidity reduction assays is indicated. The full length enzyme as reference protein is rated with '+'; multiple '+'s indicate x-fold activity compared to the full length protein; '(+)' indicates approximately half the activity of the full length protein; and constructs marked with '−' showed very low or no activity. n.d.=not determined.

FIG. 2A depicts SDS PAGE. FIG. 2B depicts a zymogram with *S. aureus* Newman cells embedded in the gel after incubation in deionized water for 60 min. FIG. 2C depicts a zymogram after incubation in deionized water for 60 min and subsequently in 10 mM Tris, 150 mM NaCl, pH 8.0 for 80 min. FIG. 2D depicts the zymogram shown in B after additional incubation in 10 mM Tris, 300 mM NaCl, pH 8.0 for 80 min. All lanes contain 5 µg of protein. Lane 1: φSH2 full length (57.4 kD); lane 2: φSH2 A1 (20.4 kD); lane 3: φSH2 B1 (38.0 kD); lane 4: φSH2 C1 (46.5 kD); lane 5: φSH2 D1 (26.1 kD); lane 6: φSH2 E1 (37.0 kD); M: Protein standard

In FIG. 4A, the highest lytic activity of each protein throughout the whole pH range was defined as 1, and in FIG. 4B, the activity at 0 mM $CaCl_2$ was defined as 1. Error bars represent standard deviations from three experiments.

DETAILED DESCRIPTION OF THE INVENTION

Figure 2:
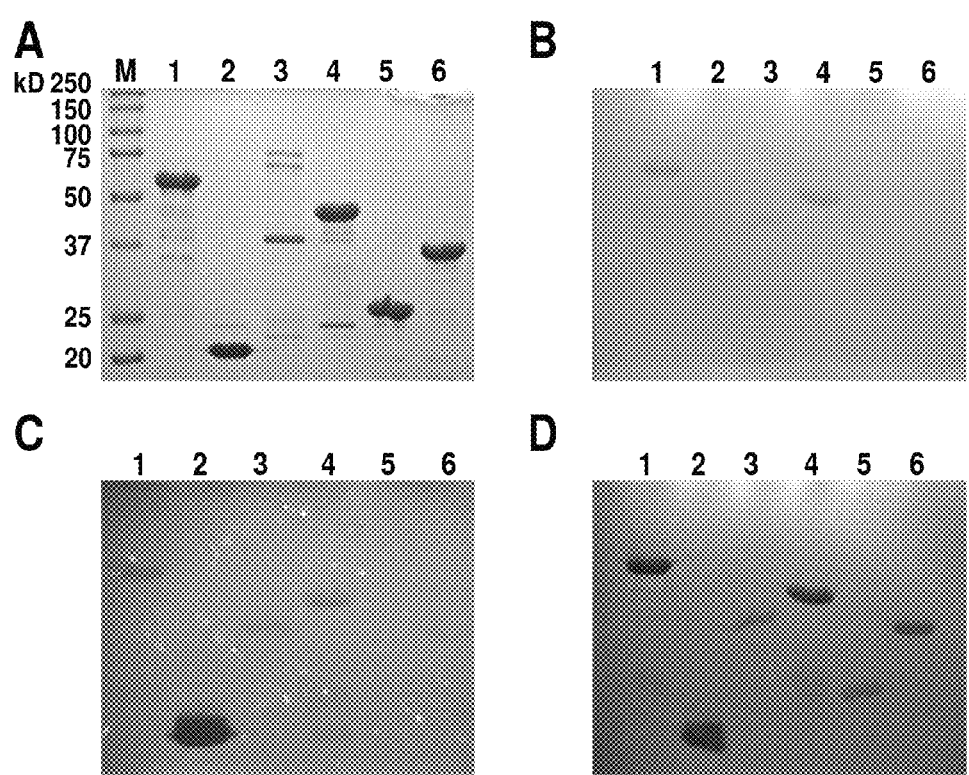
FIG. 2 depicts the SDS PAGE and zymogram analysis of the φSH2 lysin full length and deletion constructs expressed in *E. coli* and purified via Nickel affinity chromatography.

We have characterized the functional domains of *Staphylococcus haemolyticus* φSH2 endolysin and have defined the protein domains that are essential for this bactericidal activity. We have analyzed the antimicrobial lytic properties of the individual domains through deletion constructs and the resulting expressed truncated proteins in order to determine their potential in the construction of tailor-made antimicrobials for targeting the control of highly pathogenic bacteria. *S. haemolyticus* φSH2 lysin consists of two enzymatically active domains and one C-terminal cell wall binding domain. Domain database searches indicate a CHAP (Cysteine, Histidine-dependent Amidohydrolase/Peptidase) domain, an Amidase_2 domain (N-acetylmuramoyl-L-alanine amidase) in the center, and a bacterial SH3 domain (SH3b domain), which is associated with cell wall binding, at the C-terminus of the protein. Although the φSH2 lysin shares this domain architecture with a number of other staphylococcal lysins described so far, the φSH2 lysin did not reveal high homology to any other protein. The lack of sequence homology with domains of other lysins having a similar overall structure could indicate different characteristics which would be advantageous in forming new tailor-made antimicrobials.

When aiming to create antimicrobials based on peptidoglycan hydrolases by combining enzymatic and cell wall binding domains from different sources, the identification of potent functional modules is a first important step towards this goal. The *S. haemolyticus* φSH2 endolysin characterized in this study exhibits lytic activity 'from without' against *S. aureus* cells (including a MRSA strain) in three different in vitro assays and therefore, is an interesting potential source of such functional domains that could be utilized in modular fusion constructs directed against this important human and animal pathogen.

To more fully define the sequences responsible for these antimicrobial activity of the φSH2 lysin, we have created a series of deletion constructs that isolates each domain in a separate construct in an effort to compare their activity alone and when fused pairwise to the other domains in this protein. Our results suggest that the CHAP domain is the most active lytic domain during lysis from without, and that the SH3b domain is important for activity of the full length protein. However, as with any deletion construct, our findings might be complicated by incorrect folding of the truncated proteins. For instance, similar to the low solubility problems encountered with many of the constructs made in this study that extend across inter-domain regions, and which are supposedly due to misfolding of the proteins, also the low solubility and activity of our CHAP-SH3b fusions may be caused by incorrect folding of these specific constructs rather than general incompatibility of the two domains. This is backed by the finding that the CHAP-SH3b construct B1 showed a lytic band in the zymogram, which could be caused by active intermediate products formed during the refolding process within the gel, as opposed to a presumably misfolded and inactive end product which is analyzed in turbidity reduction assays. Except for the isolated CHAP domain construct A1, which showed the most intense lytic band of all tested constructs in a zymogram after incubation in a 150 mM salt buffer, all other proteins displayed their highest activity after incubation at 300 mM NaCl, which could be due to better refolding and/or higher enzymatic activity under these conditions. Some protein preparations yielded minor lytic bands in the zymogram in addition to the dominant bands caused by the φSH2 constructs (e.g., lane 4 in FIG. 2 D). This can likely be explained my small amounts of degradation products or co-purified proteins in this highly sensitive assay.

Turbidity reduction assays with the φSH2 lysin and selected deletion constructs revealed that the CHAP domain obviously plays a crucial role in the lytic activity of this endolysin when applied externally. In contrast, the amidase domain showed activity only in the presence of the SH3b domain, which was still clearly lower than that of the full length enzyme or the CHAP domain. This is consistent with findings of Becker et al. (2009b, supra) and Horgan et al. (2009. *Appl. Environ. Microbiol.* 75:872-874) who describe a similar finding with LysK, a staphylococcal phage lysin sharing the same architecture as the φSH2 endolysin. However, for LysK, the activity of the CHAP domain was enhanced by addition of an SH3b domain (Becker et al. 2009a, supra), which was not the case for the φSH2 lysin. The CHAP domain dominance pattern also holds true for the *S. aureus* φ11 phage lysin LytA (Donovan et al. 2006c. *FEMS Microbiol. Lett.* 265:133-139) (also here, the SH3b domain was shown to increase activity of the CHAP and also the amidase domain (Sass and Bierbaum. 2007. *Appl. Environ. Microbiol.* 73:347-352)), the *Staphylococcus warneri* M phage φWMY lysin (Yokoi et al., supra) and the *Streptococcus agalactiae* phage B30 endolysin (Donovan et al. (2006b. *Appl. Environ. Microbiol.* 72:5108-5112). Low et al. linked the dependence of enzymatically active domain activity on the presence of the respective cell wall binding domain to the net charge of the catalytic domain, with positively charged enzymatically active domains functioning independently of a binding domain (Low et al. 2011. *J. Biol. Chem.* 286: 34391-34403). The CHAP domain of the φSH2 endolysin features a positive net charge at pH 7.5 (+6; data not shown), and therefore the high activity of the isolated domain is in agreement with this observation.

Turbidity reduction assays with varying NaCl concentrations revealed that the A1 construct exhibits optimum activity at lower ionic strength than the full length φSH2 endolysin. A similar effect has been described for the group B streptococcal lytic enzyme PlyGBS, which consists of an N-terminal endopeptidase, a muramidases domain, and a putative C-terminal cell wall binding domain (Cheng and Fischetti. 2007. *Appl. Microbiol. Biotechnol.* 74:1284-1291). Here, a deletion construct containing only the endopeptidase domain showed 25-fold higher activity than the full length enzyme and displayed optimum activity shifted towards lower salt concentrations. Also for LysK, the isolated CHAP domain displayed higher activity at low salt concentrations (Fenton et al. 2011. *J. Appl. Microbiol.* 111:1025-1035), in contrast to the complete endolysin (Becker et al. 2008. *FEMS Microbiol. Lett.* 287:185-191). This effect can be explained by reduced binding affinity of a single domain compared to a full length enzyme including a cell wall binding domain. Also for the staphylococcal phage 187 and Twort endolysins and the *Listeria* phage endolysin Ply511, higher activity was reported for single domain containing N-terminal portions than for the complete proteins (Gaeng et al. 2000. *Appl. Environ. Microbiol.* 66:2951-2958; Loessner et al. 1998. *FEMS Microbiol. Lett.* 162:265-274; Loessner et al. 1999. *J. Bacteriol.* 181: 4452-4460). However, in these studies lytic activity was not quantified, but was defined based on the size of lysis zones in overlay assays with *S. aureus* or *Micrococcus luteus*. Therefore, the observed effect may be explained by better diffusion of the smaller deletion constructs compared to the full length proteins.

Another important finding with the φSH2 lysin is the reduction in lytic activity of the full length enzyme and the amidase domain resulting from a deletion of the SH3b domain. This is consistent with the requirement for a cell wall binding domain for full lytic activity of the bacteriocin Lysostaphin (Baba and Schneewind, 1996) and its homologue ALE-1 (Lu et al. 2006. *J. Biol. Chem.* 281:549-558), LytA from phage φ11 (Donovan et al. 2006c, supra), the *Listeria* phage endolysins Ply118 and Ply500 (Loessner et al. 2002. *Mol. Microbiol.* 44:335-349), and the LambdaSa2 prophage endolysin where the activity of the isolated endopeptidase domain is reduced in the absence of a cell wall binding domain (Becker et al. 2009b, supra). Also for the B30 lysin, the glycosidase domain was active only in combination with an SH3b domain (Donovan et al. 2006b, supra).

It should be emphasized that all results presented here describe a 'lysis from without' situation, whereas in a natural environment, the phage endolysin accesses the peptidoglycan from within the phage's host cell. This being said, the higher activity of the CHAP domain found in this study could be due to better accessibility of the peptidoglycan, which is usually shielded by multiple surface-associated molecules from the outside, by the small CHAP domain molecule compared to the larger full length lysin, whereas the latter may work equally well or better from within the cell. Also, a highly diffusible small molecule with high activity may not be beneficial for the phage due to the collateral damage in uninfected cells it would cause after lysis of the host cell (Loessner et al. 2002, supra). Effects of different surface structures such as capsules and teichoic acids, which may show strain-specific variations, on accessibility of the substrate from without may also explain the differences in susceptibility of the various *S. aureus* strains to the φSH2 constructs observed here. Furthermore, there was a trend that the full length φSH2 lysin is more effective against the coagulase-negative staphylococci than the CHAP domain construct in plate lysis assays. This could be explained by the fact that the peptidoglycan of coagulase negative species differs from that of *S. aureus* mainly within the inter-peptide bridge (Schleifer and Kandler, supra), which may affect the activity of the CHAP domain against these organisms. (The CHAP domains of LysK and LytA have been demonstrated to cleave the D-Ala-Gly bond between the stem peptide and the pentaglycin bridge of *S. aureus* peptidoglycan (Becker et al. 2009a, supra; Navarre et al. 1999. *J. Biol. Chem.* 274:15847-15856)).

It has been reported that different quantitative results can be obtained from multiple lytic activity assays with the same enzymes (Kusuma and Kokai-Kun. 2005. *Antimicrob. Agents Chemother.* 49:3256-3263). This may explain, for instance, why the A1 construct did not cause a lytic band in the zymogram after incubation in water, whereas it had considerable lytic activity at 0 mM salt in a turbidity reduction assay; why the full length protein did not lyse *S. aureus* strain Newman in a plate lysis assay at the highest concentration tested, whereas it showed activity in turbidity reduction assays against the same strain; or why the B1 and D1 constructs displayed only background levels of activity in the turbidity reduction assay, whereas they yielded cleared bands in the zymogram. An alternative explanation for the difference in activity of the A1 construct at 0 mM NaCl between the zymogram and the turbidity reduction assay may be that water provides suboptimal re-folding conditions for A1, so that it does not assume a functional conformation.

Enhancement of lytic activity by low concentrations of bivalent metal cations as observed for the full length φSH2 lysin and the A1 construct has been described previously for a number of different peptidoglycan hydrolases, such as the φ11 endolysin LytA (Donovan et al. 2006c, supra) and the streptococcal phage B30 endolysin (Pritchard et al. 2004. Microbiology 150:2079-2087), which both displayed optimum activity in presence of 3 mM and 10 mM $Ca^{2+}$, respectively. This is an advantageous property of an enzyme when considering an application as antimicrobial against mastitis-causing pathogens in a milk environment (the concentration of available $Ca^{2+}$ in milk is approximately 3 mM).

The idea of using peptidoglycan hydrolases against mastitis causing pathogens is not new. Lysostaphin has been used successfully for preventing *Staphylococcus aureus* mammary infection in transgenic mice (Kerr et al. 2001. *Natl. Biotechnol.* 19:66-70) and cattle (Wall et al. 2005. *Natl. Biotechnol.* 23:445-451). Even though these results are encouraging, it is known that Lysostaphin has a single endopeptidase domain which cleaves within the pentaglycine crossbridge (Browder et al. 1965. *Biochem. Biophys. Res. Commun.* 19:389). As mentioned above, this is the least conserved portion of the peptidoglycan, and mutant strains with alterations in their peptidoglycan crossbridges that render them resistant to Lysostaphin have been described. In contrast, many staphylococcal bacteriophage endolysins including the φSH2 lysin feature two different enzymatically active domains, which is anticipated to make resistance formation a rare event, as one bacterial cell would likely require two simultaneous compensatory mutations (Fischetti 2005, supra). This reduced chance of resistance formation as well as high target cell specificity render native bacteriophage endolysins and especially chimeric constructs consisting of multiple unique and potent enzymatic domains promising alternatives to antibiotics in medical and agricultural applications. To this end, the CHAP domain of the φSH2 endolysin could be an interesting addition to the arsenal of enzymatic modules directed against pathogenic staphylococci both on the farm and in human clinical settings.

According to the present invention, the terms "nucleic acid molecule", "nucleic acid sequence", "polynucleotide", "polynucleotide sequence", "nucleic acid fragment", "isolated nucleic acid fragment" are used interchangeably herein. These terms encompass nucleotide sequences and the like. A polynucleotide may be a polymer of RNA or DNA that is single- or double-stranded and that optionally contains synthetic, non-natural or altered nucleotide bases. A polynucleotide in the form of a polymer of DNA may be comprised of one or more segments of cDNA, genomic DNA, synthetic DNA, or mixtures thereof. This will also include a DNA sequence for which the codons encoding the φSH2 prophage endolysin according to the invention will have been optimized according to the host organism in which it will be expressed, these optimization methods being well known to those skilled in the art.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. However, isolated polynucleotides may contain polynucleotide sequences which may have originally existed as extrachromosomal DNA but exist as a nucleotide insertion within the isolated polynucleotide. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "transgene" is understood to describe genetic material which has been or is about to be artificially inserted into the genome of a non-human animal, and particularly into a cell of a living non-human mammal. It is to be understood that as used herein the term "transgenic" includes any cell, cell line, or tissue, the genotype of which has been altered by the presence of a heterologous nucleic acid including those transgenics initially so altered as well as those created by sexual crosses or asexual propagation from the initial transgenic.

The term "transformation" refers to a permanent or transient genetic change induced in a cell following the incorporation of new DNA (i.e. DNA exogenous to the cell). Where the cell is a mammalian cell, a permanent genetic change is generally achieved by introduction of the DNA into the genome of the cell. When the cell is a bacterial cell, the term usually refers to an extrachromosomal, self-replicating vector which harbors a selectable antibiotic resistance. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell.

The term "construct" refers to a recombinant nucleic acid, generally recombinant DNA, that has been generated for the purpose of the expression of a specific nucleotide sequence(s), or is to be used in the construction of other recombinant nucleotide sequences. A "construct" or "chimeric gene construct" refers to a nucleic acid sequence encoding a protein, operably linked to a promoter and/or other regulatory sequences.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter) or a DNA sequence and a regulatory sequence(s) are connected in such a way as to permit gene expression when the appropriate molecules (e.g., transcriptional activator proteins) are bound to the regulatory sequence(s).

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter.

The term "cDNA" refers to all nucleic acids that share the arrangement of sequence elements found in native mature mRNA species, where sequence elements are exons and 3' and 5' non-coding regions. Normally mRNA species have contiguous exons, with the intervening introns removed by nuclear RNA splicing, to create a continuous open reading frame encoding the protein. "cDNA" refers to a DNA that is complementary to and derived from an mRNA template.

The term "genomic sequence" refers to a sequence having non-contiguous open reading frames, where introns interrupt the protein coding regions. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence.

As used herein, "recombinant" refers to a nucleic acid molecule which has been obtained by manipulation of genetic material using restriction enzymes, ligases, and similar genetic engineering techniques as described by, for example, Sambrook et al. 1989. Molecular Cloning: A Laboratory Manual, Second Edition, Cold Spring Harbor Laboratory Press, Cold Spring Harbor, N.Y. or DNA Cloning: A Practical Approach, Vol. I and II (Ed. D. N. Glover), IRL Press, Oxford, 1985. "Recombinant," as used herein, does not refer to naturally occurring genetic recombinations.

As used herein, the term "chimeric" refers to two or more DNA molecules which are derived from different sources, strains, or species, which do not recombine under natural conditions, or to two or more DNA molecules from the same species, which are linked in a manner that does not occur in the native genome.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

A "protein" or "polypeptide" is a chain of amino acids arranged in a specific order determined by the coding sequence in a polynucleotide encoding the polypeptide. Each protein or polypeptide has a unique function.

The invention includes functional φSH2 prophage endolysin polypeptide and functional fragments thereof, as well as mutants and variants having the same biological function or activity. As used herein, the terms "functional fragment", "mutant" and "variant" refers to a polypeptide which possesses biological function or activity identified through a defined functional assay and associated with a particular biologic, morphologic, or phenotypic alteration in the cell. The term "functional fragments of φSH2 endolysin" refers to all fragments of φSH2 endolysin that retain φSH2 phage endolysin activity and function to lyse staphylococcal bacteria.

Modifications of the φSH2 prophage endolysin primary amino acid sequence may result in further mutant or variant proteins having substantially equivalent activity to the φSH2 prophage endolysin polypeptides described herein. Such modifications may be deliberate, as by site-directed mutagenesis, or may occur by spontaneous changes in amino acid sequences where these changes produce modified polypeptides having substantially equivalent activity to the φSH2 prophage endolysin polypeptide. Any polypeptides produced by minor modifications of the φSH2 prophage endolysin primary amino acid sequence are included herein as long as the biological activity of φSH2 prophage endolysin is present; e.g., having a role in pathways leading to lysis of staphylococcal bacteria.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. A method of selecting an isolated polynucleotide that affects the level of expression of a polypeptide in a host cell may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. Nucleic Acid Hybridization, Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. An indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein. Thus, isolated sequences that encode a φSH2 prophage endolysin polypeptide and which hybridize under stringent conditions to the φSH2 prophage endolysin sequences disclosed herein, or to fragments thereof, are encompassed by the present invention.

Substantially similar nucleic acid fragments of the instant invention may also be characterized by the percent identity of the amino acid sequences that they encode to the amino acid sequences disclosed herein, as determined by algorithms commonly employed by those skilled in this art. Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. CABIOS 4:11-17), the local homology algorithm of Smith et al. (1981. Adv. Appl. Math. 2:482); the homology alignment algorithm of Needleman and Wunsch (1970. J. Mol. Biol. 48:443-453); the search-for-similarity-method of Pearson and Lipman (1988. Proc. Natl. Acad. Sci. 85:2444-2448; the algorithm of Karlin and Altschul (1990. Proc. Natl. Acad. Sci. USA 87:2264), modified as in Karlin and Altschul (1993. Proc. Natl. Acad. Sci. USA 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. J. Mol. Biol. 48:443).

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise a particular plant protein. The skilled artisan, having the benefit of the sequences as reported herein, may now use all or a substantial portion of the disclosed sequences for purposes known to those skilled in this art. Thus, such a portion represents a "substantial portion" and can be used to establish "substantial identity", i.e., sequence identity of at least 80%, compared to the reference sequence. Accordingly, the instant invention comprises the complete sequences as reported in the accompanying Sequence Listing, as well as substantial portions at those sequences as defined above.

Fragments and variants of the disclosed nucleotide sequences and proteins encoded thereby are also encompassed by the present invention. By "fragment" a portion of the nucleotide sequence or a portion of the amino acid sequence and hence protein encoded thereby is intended. Fragments of a nucleotide sequence may encode protein fragments that retain the biological activity of the native protein and hence have φSH2 prophage endolysin-like activity. Alternatively, fragments of a nucleotide sequence that are useful as hybridization probes may not encode fragment proteins retaining biological activity.

By "variants" substantially similar sequences are intended. For nucleotide sequences, conservative variants include those sequences that, because of the degeneracy of the genetic code, encode the amino acid sequence of one of the φSH2 prophage endolysin polypeptides of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they possess the desired biological activity, that is, φSH2 prophage endolysin activity as described herein. Such variants may result from, for example, genetic polymorphism or from human manipulation. Biologically active variants of a native φSH2 prophage endolysin protein of the invention will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even 1 amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired φSH2 prophage endolysin activity. Obviously, the mutations that will be made in the DNA encoding the variant must not place the sequence out of reading frame and preferably will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of φSH2 prophage endolysin protein can be observed.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

The staphylococcal control compositions of the invention comprise the antimicrobial composition of the invention dissolved or suspended in an aqueous carrier or medium. The composition may further generally comprise an acidulant or admixture, a rheology modifier or admixture, a film-forming agent or admixture, a buffer system, a hydrotrope or admixture, an emollient or admixture, a surfactant or surfactant admixture, a chromophore or colorant, and optional adjuvants. The preferred compositions of this invention comprise ingredients which are generally regarded as safe, and are not of themselves or in admixture incompatible with milk or milk by-products or human and veterinary applications. Likewise, ingredients may be selected for any given composition which are cooperative in their combined effects whether incorporated for antimicrobial efficacy, physical integrity of the formulation or to facilitate healing and health in medical and veterinary applications, including for example in the case of mastitis, healing and health of the teat. or other human or animal body part. Generally, the composition comprises a carrier which functions to dilute the active ingredients and facilitates stability and application to the intended surface. The carrier is generally an aqueous medium such as water, or an organic liquid such as an oil, a surfactant, an alcohol, an ester, an ether, or an organic or aqueous mixture of any of these. Water is preferred as a carrier or diluent in compositions of this invention because of its universal availability and unquestionable economic advantages over other liquid diluents.

Avoiding the generalized use of broad range antimicrobials and using highly specific antimicrobials for just the target organisms involved, should help reduce the ever-increasing incidence of antibiotic resistance.

EXAMPLES

Having now generally described this invention, the same will be better understood by reference to certain specific examples, which are included herein only to further illustrate the invention and are not intended to limit the scope of the invention as defined by the claims.

Example 1

Plasmids, Constructs and Strains

The *Staphylococcus haemolyticus* JCSC1435 lysin (GenBank Accession Number BAE05642.1) nucleotide sequence was obtained from the genomic sequence of *S. haemolyticus* JCSC1435 (Takeuchi et al., supra; Genbank Accession Number: NC_007168. The open reading frame was synthesized (GeneArt, Regensburg, Germany) with an *E. coli*-optimized codon bias and inserted into pET21a (EMD Biosciences, San Diego, Calif.) using conventional molecular techniques. The plasmid construct contains the lysin gene between the NdeI and XhoI restriction sites and encodes a C-terminally 6×His-tagged version of the protein. The truncations of the φSH2 gene were created by standard molecular biological methods. Gene fragments were amplified by PCR as previously described (Donovan and Foster-Frey. 2008. *FEMS Microbiol. Lett.* 287:22-33) using the full length φSH2 construct (in pET21a) as template and the primers shown in Table 1, that by design add NdeI and XhoI sites to the 5' and 3' ends of each fragment, respectively. PCR products were NdeI and XhoI digested and inserted into similarly digested pET21a. The φSH2 B1 and B2 constructs were created by inserting a SH3b cell wall binding domain, encoding PCR-derived DNA fragments with XhoI restriction sites on both ends, into the XhoI site of p φSH2_A1 and p φSH2_A3, respectively.

TABLE 1

Plasmids and Primers

| Plasmids | Proteins produced | Forward primer | Reverse primer | Recipient Vector |
|---|---|---|---|---|
| pφSH2 | φSH2 complete (1-493) | | | pET21a |
| pφSH2_A1 | φSH2 A (1-166) | φSH2_NdeI_F | φSH2_166_XhoI_R | pET21a |
| pφSH2_A2 | φSH2 A1 (1-210) | φSH2_NdeI_F | φSH2_210_XhoI_R | pET21a |
| pφSH2_A3 | φSH2 A2 (1-245) | φSH2_NdeI_F | φSH2_245_XhoI_R | pET21a |
| pφSH2_A4 | φSH2 A1 (1-287) | φSH2_NdeI_F | φSH2_287_XhoI_R | pET21a |
| pφSH2_B1 | φSH2B (1-166 + 341-493) | φSH2_341_XhoI_F | φSH2_XhoI_R | pφSH2_A1 |
| pφSH2_B2 | φSH2B (1-246 + 347-493) | φSH2_347_XhoI_F | φSH2_XhoI_R | pφSH2_A3 |
| pφSH2_C1 | φSH2 C (1-397) | φSH2_NdeI_F | φSH2_397_XhoI_R | pET21a |
| pφSH2_C2 | φSH2 C (1-429) | φSH2_NdeI_F | φSH2_429_XhoI_R | pET21a |
| pφSH2_D1 | φSH2 D(178-397) | φSH2_178_NdeI_F | φSH2_397_XhoI_R | pET21a |
| pφSH2_D2 | φSH2 D(178-429) | φSH2_178_NdeI_F | φSH2_429_XhoI_R | pET21a |
| pφSH2_E1 | φSH2 E(178-493) | φSH2_178_NdeI_F | φSH2_XhoI_R | pET21a |
| pφSH2_E2 | φSH2 E(148-493) | φSH2_148_NdeI_F | φSH2_XhoI_R | pET21a |

| Primer | SEQUENCE* |
|---|---|
| φSH2_NdeI_F | 5'-CGC GCG CAT ATG AAA ACA CAA GCA-3' |
| φSH2_166_XhoI_R | 5'-CAC CAC CTC GAG AGC TAC TGG TGG AAC-3' |
| φSH2_210_XhoI_R | 5'-AC ACC TTT CTC GAG GTA ACC TCG T-3' |
| φSH2_245_XhoI_R | 5'-AAC ATA AGC CTC GAG GAT ACC ACG-3' |
| φSH2_287_XhoI_R | 5'-TC ACT TGC ACG TAA CTC GAG ATT CAC T-3' |
| φSH2_341_XhoI_F | 5'-CTC TGA CTC GAG GTG CTT CAT ACT GG-3' |
| φSH2_XhoI_R | 5'-GTG GTG CTC GAG ACT GAT TAC TCC-3' |
| φSH2_347_XhoI_F | 5'-GTG CTT CAT ACT CTC GAG GAT CCG TTG-3' |
| φSH2_397_XhoI_R | 5'-GAC CAC CTC GAG TTT ACG TGT AGC TGG-3' |
| φSH2_429_XhoI_R | 5'-T ATT TGT GAA CTC GAG AAC GTA ACG-3' |
| φSH2_178_NdeI_F | 5'-AGT ATC AAC ACA TAT GCA AGC ACC TAA ACA AAA AG-3' |
| φSH2_148_NdeI_F D.N. 0171.09 | 5'-CTA ATA AGC ATA TGA GCC TAC GTT GG-3' |

*The primer sequences are identified by SEQ ID NOs: 26-37, respectively.

A series of deletion constructs of the φSH2 lysin were created in order to determine the contribution of each lytic domain to the lytic activity of the enzyme (FIG. 1). All constructs contained eight additional amino acids at their C-termini, consisting of Leu-Glu (which is introduced by the XhoI restriction enzyme recognition sequence) and the 6×His-tag used for nickel chromatography during protein purification. All subcloning was performed in *E. coli* DH5α, and all constructs were verified by sequencing. *E. coli* BL21 (DE3) was used for expression of proteins. All *E. coli* strains were grown in Luria-Bertani (LB) medium, with addition of 150 μg/ml ampicillin for plasmid selection. *Staphylococcus aureus* strain Newman (NCTC8178) was used for turbidity reduction assays, plate lysis assays, and zymograms, after culturing at 37° C. to mid-log phase growth in tryptic soy broth (TSB). Other *S. aureus* and coagulase negative staphylococcal (CoNS) strains used for plate lysis assays (listed in Table 2) were cultured the same way. Strain 305 (Newbould) was purchased from the American Type Culture Collection (ATCC 29740). The Tanji strains (mastitis isolates) were obtained as a gift from Yasunori Tanji (Tokyo Institute of Technology; Synnott et al. 2009. *Appl. Environ. Microbiol.* 75:4483-4490). The NRS strains (MRSA strains) were obtained from NARSA (Eurofins Medinet, Inc., Chantilly, Va.). All CoNS strains are mastitis isolates and were obtained from Max Paape (ARS, Beltsville, Md.), except for *Staphylococcus hyicus*, obtained from David Kerr (University of Vermont).

The nucleic acid molecules encoding the full length φSH2 lysin (SEQ ID NO:1) and deletion constructs: pφSH2_A1 (SEQ ID NO:3), pφSH2_A2 (SEQ ID NO:5), pφSH2_A3 (SEQ ID NO:7), pφSH2_A4 (SEQ ID NO:9), pφSH2_B1 (SEQ ID NO:11), pφSH2_B2 (SEQ ID NO:13), pφSH2_C1 (SEQ ID NO:15), pφSH2_C2 (SEQ ID NO:17), pφSH2_D1 (SEQ ID NO:19), pφSH2_D2 (SEQ ID NO:21), pφSH2_E1 (SEQ ID NO:23), and pφSH2_E2 (SEQ ID NO:25) comprise nucleotides encoding C-terminal LE,HHHHHH residues. The full length and truncated proteins (FIG. 1) encoded by these nucleic acid sequences are identified by SEQ ID NOs: 2, 4, 6, 8, 10, 12, 14, 16, 18, 20, 22, 24, and 26, respectively. The expressed proteins are His-tagged with eight additional amino acid residues introduced at the C-terminus corresponding to the XhoI site (Leu-Glu) followed by six His residues.

Example 2

Protein Expression, Purification and Analysis

*E. coli* BL21 (DE3) cultures harboring pET21a-derived expression vectors were grown to mid log phase ($OD_{600\,nm}$ of 0.4-0.6) under ampicillin selection, chilled on ice for 30 min, induced with 1 mM IPTG, and incubated with shaking for 18 h at 19° C. For protein purification under native conditions, cells from 800 mL cultures were harvested by centrifugation, resuspended in 16 mL of Lysis Buffer (50 mM $NaH_2PO_4$, 300 mM NaCl, 10 mM imidazole, 30% glycerol, pH 8.0), sonicated on ice for 5 min (1 s pulses separated by 1 s rests), and centrifuged at 9000×g for 30 min. The cleared supernatant containing the soluble form of the target proteins was applied to 1 mL nickel-NTA-Superflow resin (QIAGEN, Valencia, Calif.) and rotated for 1 h at 4° C. The nickel matrix was packed into empty chromatography columns (QIAGEN) and washed with 20 mL of Lysis buffer, followed by 20 mL of Wash Buffer (50 mM $NaH_2PO_4$, 300 mM NaCl, 20 mM imidazole, 30% glycerol, pH 8.0). Target proteins were eluted with 2 mL of elution buffer (50 mM $NaH_2PO_4$, 300 mM NaCl, 250 mM imidazole, 30% glycerol, pH 8.0). The buffer was exchanged to 20 mM $NaH_2PO_4$, 150 mM NaCl, 30% glycerol, pH 7.5 using 5 mL ZEBA desalting columns (Thermo Fisher Scientific, Rockford, Ill.), and protein preparations were 0.22-μm filter sterilized and stored at 4° C. until used.

For protein purification under denaturing conditions, pellets from induced cultures were resuspended in 16 mL buffer B (100 mM $NaH_2PO_4$, 10 mM Tris, 8 M urea, pH 8.0) per 800 mL culture and incubated at room temperature for 60 min under agitation in order to disrupt the cells and dissolve putative inclusion bodies. Residual insoluble material was eliminated by centrifugation for 25 min at 1000×g. The supernatant was applied to Ni-NTA resin and packed into a column as described above. The column was washed with 20 ml buffer C (100 mM $NaH_2PO_4$, 10 mM Tris, 8 M urea, pH 6.3) and target proteins were eluted with 2 ml of buffer E (100 mM $NaH_2PO_4$, 10 mM Tris, 8 M urea, pH 4.5). Eluted fractions were dialyzed against 20 mM $NaH_2PO_4$, 150 mM NaCl, 15% glycerol, pH 7.5 using Spectra/Por tubing (MWCO 12000-14000; Spectrum Laboratories Inc., Rancho Dominguez, Calif.), 0.22-μm filter sterilized, and stored at 4° C. until use. Concentrations of all protein preparations were determined spectrophotometrically using a NanoDrop ND-1000 device (NanoDrop Technologies, Wilmington, Del.).

A series of deletion constructs of the φSH2 lysin were created in order to determine the contribution of each lytic domain to the lytic activity of the enzyme (FIG. 1). These include a series of constructs comprising the complete putative CHAP domain and portions of increasing length of the linker region between the CHAP and the amidase domain, as well as the N-terminal end of the amidase domain (A1-A4); two versions of the CHAP domain (with and without a portion of the amidase domain) fused to the SH3b cell wall binding domain (B1, B2); and two different length variants each of the CHAP plus the amidase domain (C1, C2), the isolated amidase domain (D1, D2), and the amidase plus the SH3b domain (E1, E2). When purified under native conditions, mostly those constructs comprising only complete functional domains and no partial domains yielded high concentrations (>0.5 mg/ml) and purities (as shown for the full length protein and the A1, C1, D1, and E1 constructs in FIG. 2 A, and indicated in the 'Purification' column in FIG. 1). Within the CHAP series (A1-A4), solubility decreased with increasing length of the constructs and extension across the inter-domain region. For the B1 construct, which is a fusion of the intact φSH2 CHAP and SH3b domains (see FIG. 2 A, lane 3), as well as the A3, D2, and E2 constructs, which all contain fractions of functional domains, lower concentrations (<0.5 mg/ml) were obtained, and preparations were of lower purity. The A4, B2, and C2 constructs did not yield any detectable soluble protein when purified under native conditions, but under denaturing conditions, they were obtained in the elution fraction at concentrations >1 mg/ml, suggesting that they were present as inclusion bodies in the *E. coli* cells (data not shown). However, all three constructs completely precipitated during subsequent dialysis, and no soluble protein could be recovered for determination of lytic activity. Mostly those constructs that extended beyond inter-domain regions yielded low concentrations when purified under native conditions and showed very low or no lytic activity against staphylococcal cells in turbidity reduction assays (as indicated in the 'Activity' column in FIG. 1; data not shown). Therefore, for each group of constructs, the protein that yielded the highest concentration under native purification conditions and contained only intact functional domains (A1, B1, C1, D1, and E1; subsequently referred to as the 'selected constructs') was selected for further characterization in zymograms and turbidity reduction assays in comparison with the full length φSH2 lysin, whereas characterization of all other constructs was not further pursued.

All purified proteins were analyzed with 15% SDS-PAGE, using a Kaleidoscope Precision Plus Protein Standard (Bio-Rad, Hercules, Calif.). For zymograms, a 300 mL culture volume equivalent of live mid-log phase ($OD_{600nm}$=0.4-0.6) cells of *S. aureus* strain Newman was embedded in the gel during polymerization. The protein samples were boiled in Laemmli sample buffer (BioRad) with β-mercaptoethanol, and electrophoresed with identical buffers and voltage for one hour in both the SDS-PAGE and the zymogram using a Mini-Protean TETRA gel system (BioRad). SDS gels were Coomassie stained and zymograms were washed in excess water and further incubated in deionized water for 60 min, followed by incubation in 10 mM Tris, pH 8.0 with 150 mM or 300 mM NaCl for 80 min. Areas of clearing in the turbid zymogram gel indicate a lytic protein in the gel.

In zymograms impregnated with *S. aureus* Newman cells, the full length φSH2 lysin as well as those constructs containing a CHAP and additionally either an SH3b or an amidase domain (B1 and C1) showed faint zones of lysis after incubation in deionized water for 60 min (FIG. 2 B). When further incubated in buffer containing 150 mM NaCl for up to 80 min, the A1 construct (isolated CHAP domain) developed an intense lytic band, whereas lysis zones of the full length φSH2 and the B1 and C1 constructs remained considerably weaker, and the E1 construct (amidase plus SH3b) caused only very faint lysis (FIG. 2 C). When the zymogram was incubated in buffer containing 300 mM NaCl following incubation in water, also the D1 construct (isolated amidase domain) showed a pronounced lytic band, as did all other selected constructs and the full length φSH2 lysin (FIG. 2 D).

Example 4

Turbidity Reduction Assay

The turbidity reduction assay measures a decrease in optical density of a bacterial suspension due to lysis of the target bacteria by a lytic protein. The assays were performed in a 96-well dish format essentially as described previously (Donovan et al. 2006, supra). In order to reduce the variability of the assay, frozen stocks of S. aureus Newman substrate cells were prepared in a large batch as described by Becker et al. (2009b, supra). Immediately prior to the assay, the frozen cells were thawed, washed, and resuspended in the desired assay buffer such that when 100 µl of cell suspension were added to 100 µl of lysis buffer+/−protein, the final suspension has an $OD_{600nm}$ of ~1.0.

Protein constructs were assayed at a concentration of 1 µM, and the assay was performed at room temperature, measuring the $OD_{600nm}$ at 1 min intervals for 45 min. Buffer without enzyme served as the control. The steepest slopes of the resulting lysis curves, which correspond to the lytic activities of the proteins, were determined by a sliding window over each group of three consecutive time points for the entire 45 min period. Specific activities were expressed as $\Delta OD_{600nm}$/min/µM, and the "no enzyme" control value was subtracted from each experimental value.

In order to determine the effect of salt concentration on lytic activity, turbidity reduction assays were performed in 10 mM Tris buffers at pH 7.5 with varying NaCl concentrations between 0 mM and 600 mM. Accordingly, the influence of pH was determined by using a series of different buffers with pH values ranging from 3.5 to 10.0. Citrate buffers were used for pH 3.5, 4.5, 5.5, and 6.0, MOPS buffers for pH 6.5, 7.0, and 7.5, Tris buffers for pH 8.0 and 9.0, and Carbonate/bicarbonate buffer for pH 10.0. The concentration of the buffer substance in all buffers used was 20 mM, and the NaCl concentration was 200 mM. To test the effect of bivalent metal ions, assays were performed in 10 mM Tris, 200 mM NaCl, pH 7.5 supplemented with $MgCl_2$, $MnCl_2$, or $CaCl_2$ at different concentrations (0.1 mM, 1 mM, 10 mM), buffer without metal ions serving as control.

Figure 3:
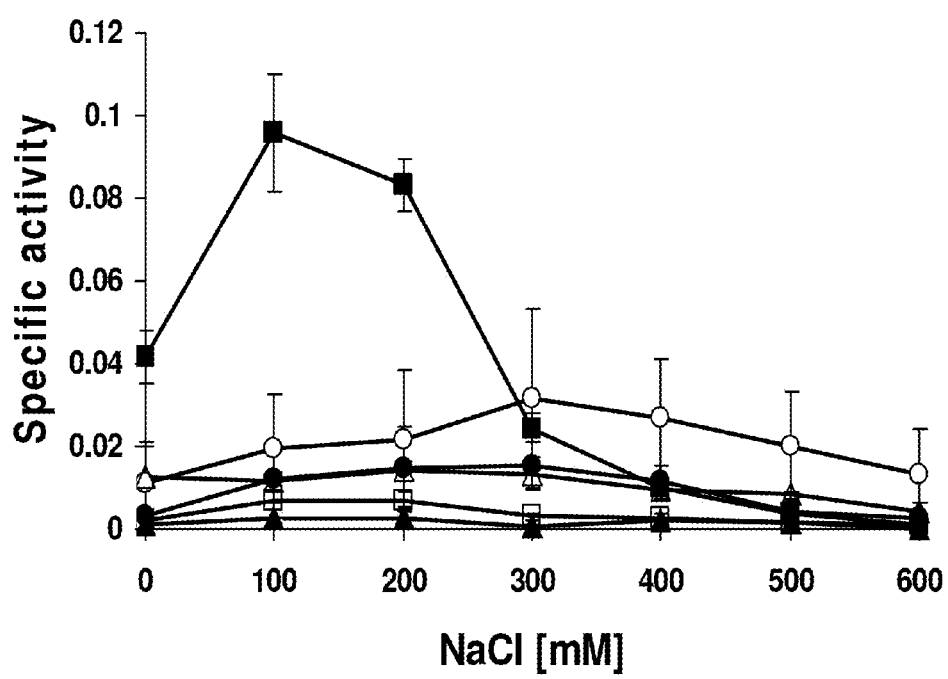
FIG. 3 depicts lytic activities of the φSH2 full length endolysin and deletion constructs against *Staphylococcus aureus* Newman cells at different salt concentrations. Turbidity reduction assays were performed with φSH2 full length endolysin (open circles), φSH2 A1 (black squares), φSH2 B1 (black triangles), φSH2 C1 (open triangles), φSH2 D1 (open squares), and φSH2 E1 (black circles) at identical molar concentrations (1 µM). Specific activities are expressed as $\Delta OD_{600nm}/min/\mu M$. Error bars represent standard deviations from three experiments.

The zymogram findings are consistent with the results of turbidity reduction assays performed at different salt concentrations with equimolar concentrations of the selected constructs, using S. aureus Newman as substrate cells (FIG. 3). Whereas the full length φSH2 lysin showed moderate lytic activity over the whole range of tested NaCl concentrations with optimum activity at 300 mM, the isolated CHAP domain (A1) displayed a more pronounced optimum of activity between 100 mM and 200 mM NaCl. Interestingly, the specific activity of the CHAP domain at its optimum salt concentration was approximately three-fold higher than that of the full length enzyme. This is in accordance with the zymogram, where the A1 construct caused the most prominent lysis zone of all proteins. In contrast, all other deletion constructs exhibited considerably weaker activity than the full length lysin in turbidity reduction assays, suggesting that the enzyme mainly relies on the CHAP domain activity during lysis from without.

While the CHAP domain alone showed the highest lytic activity of all constructs tested in this study, the addition of an SH3b domain to its C-terminus (in the B1 construct) not only markedly reduced its solubility (see FIG. 1), but also completely abolished its activity (FIG. 3). Also the C1 construct, which combines both enzymatic domains but lacks the SH3b cell wall binding domain, showed drastically reduced activity compared to the CHAP domain alone, and the activity was similar over a wider range of NaCl concentrations, similar to the full length φSH2 lysin. The full length lysin, however, which differs from the C1 construct only by the presence of the C-terminal SH3b domain, was about twice as active at its optimum salt concentration. This also holds true for the amidase domain. Whereas the D1 construct (isolated amidase domain) showed only background levels of activity in turbidity reduction assays, the addition of an SH3b domain (E1 construct) increased the activity to approximately the same level as the C1 construct, i.e. about half the activity of the full length φSH2 lysin, with a similar salt optimum curve. Overall, these results suggest that the cell wall binding domain is required for full activity of the amidase domain and the complete φSH2 lysin, but the function of the CHAP domain in a lysis from without setting is impaired by the addition of a further enzymatic or SH3b domain.

Figure 4:
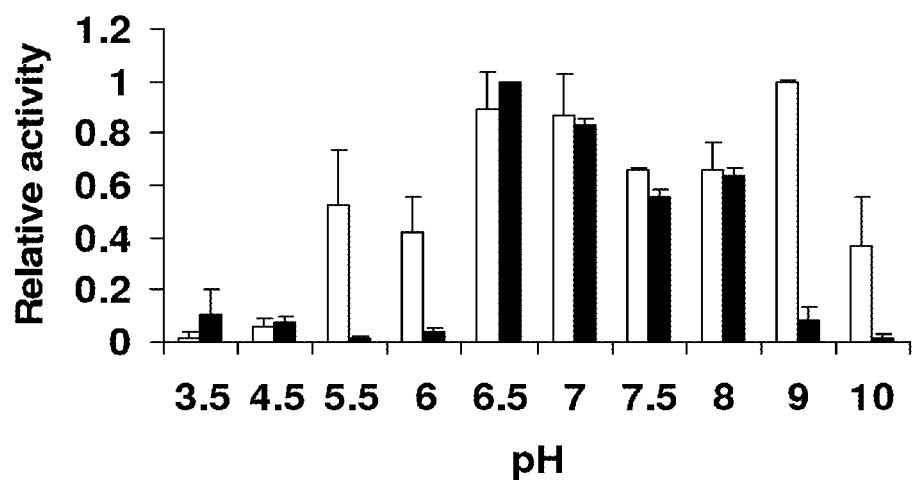
FIG. 4 depicts lytic activities of the φSH2 full length endolysin and the φSH2 A1 construct against *Staphylococcus aureus* Newman cells at different pH (FIG. 4A) and $CaCl_2$ concentrations (FIG. 4B). Turbidity assays were performed with identical molar amounts (1 µM) of each protein. Relative activities of φSH2 full length (white bars) and φSH2 A1 (black bars) are shown.
Figure 4:
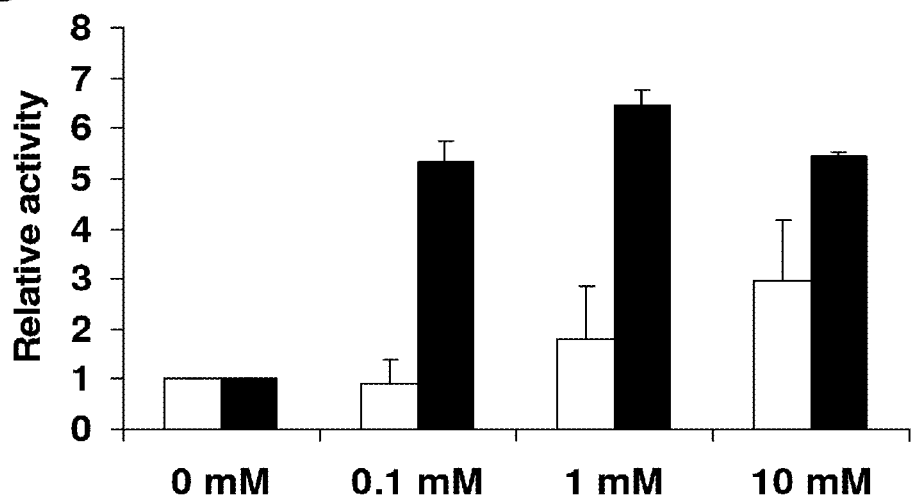

The full length φSH2 lysin and the A1 construct were characterized further in the turbidity reduction assays, investigating the effect of pH and the presence of various bivalent metal ions on their activity against S. aureus Newman cells. While the complete enzyme showed a higher tolerance to different pH conditions, exhibiting lytic activity in different buffer systems between pH 5.5 and 10, with highest activity between pH 6.5 and 9, the activity range of the CHAP domain was found to be narrower, with activity dropping to background levels below pH 6.5 and above pH 8 (FIG. 4 A). Regarding the effect of bivalent metal ions, $Mg^{2+}$ was found to not significantly alter the lytic activity of the full length enzyme and the CHAP domain at the concentrations tested (0.1-10 mM), and $Mn^{2+}$ had a slightly inhibitory effect (data not shown). In contrast, $Ca^{2+}$ increased the activity of the full length φSH2 lysin three-fold (at a concentration of 10 mM), and that of the A1 construct more than 6-fold (at a concentration of 1 mM) (FIG. 4 B).

Example 5

Plate Lysis Assay

Purified proteins (100 pmoles in a 10 µl volume and five two-fold serial dilutions thereof) were spotted onto a freshly spread lawn of log phase staphylococcal cells ($OD_{600\,nm}$ of 0.4-0.6, diluted ¼ before plating) that had air dried for 15 min on gridded TSA (tryptic soy agar) plates. The spotted plates were air dried for 10 min in a laminar flow hood and incubated overnight at 37° C. Cleared spots indicating cell lysis were scored within 24 hours of plating the cells. Staphylococcal strains used for plate lysis are shown in Table 2.

The φSH2 full length enzyme and the A1 construct were further tested in plate lysis assays against a set of different staphylococcal strains, including MRSA strains (NRS 382-385), mastitis isolates (305, Tanji 1-26), and coagulase negative staphylococci (non S. aureus) (Table 2). The same molar amounts of both proteins (ranging from 100 pmoles to 3.125 pmoles, in a volume of 10 ul) were spotted onto lawns of mid log phase cells of the respective strains, and the plates were analyzed for lysis zones the next day. *S. aureus* strain Newman, which was used as a reference strain, was not lysed by the highest amount of full length enzyme tested, but 100 pmoles of the A1 construct caused a lysis zone on this strain. For all mastitis and MRSA strains, the CHAP construct showed equal or higher activity (i.e. caused a clearing at a lower amount) than the parental full length φSH2 lysin. Whereas all mastitis isolates were lysed by both proteins within the range of amounts tested, the full length enzyme showed activity against only one out of four MRSA strains, and the A1 construct lysed two MRSA strains at 50 pmoles. Regarding the CoN strains, mostly the φSH2 full length showed higher activity than the A1 construct, except for *S. simulans*, which was lysed by 25 pmoles of A1, as opposed to 100 pmoles of the parental protein. *S. hyicus* was found to be most susceptible to the action of both constructs. The full length lysin caused a lysis zones against this strain at the lowest amount tested, and the A1 construct at 12.5 pmoles. Overall, the parental enzyme displayed lytic activity against 11 out of 16 strains tested in this experimental setup, and the CHAP construct against 13 out of 16.

TABLE 2

Lytic activity of ΦSH2 full length lysin and ΦSH2 A1 in the Plate Lysis Assay.

| Strain | Lytic activity | |
|---|---|---|
| | ΦSH2 full length | ΦSH2 A1 |
| *S. aureus* Newman | − | + |
| *S. aureus* 305 | ++ | ++++ |
| *S. aureus* Tanji 1 | ++ | +++ |
| *S. aureus* Tanji 19 | ++ | +++ |
| *S. aureus* Tanji 20 | ++ | +++ |
| *S. aureus* Tanji 26 | + | + |
| *S. aureus* NRS 382 | − | ++ |
| *S. aureus* NRS 383 | − | − |
| *S. aureus* NRS 384 | + | ++ |
| *S. aureus* NRS 385 | − | − |
| *S. chromogenes* | +++ | ++ |
| *S. epidermidis* | − | − |
| *S. hyicus* | ++++++ | ++++ |
| *S. simulans* | + | +++ |
| *S. warneri* | +++ | ++ |
| *S. xylocus* | +++ | ++ |

100 pmoles and 2-fold serial dilutions thereof were spotted on bacterial lawns.
The lytic activity against each strain corresponding to the lowest amount of protein producing a lysis zone is indicated as follows.
+: 100 pmoles,
++: 50 pmoles;
+++: 25 pmoles;
++++: 12.5 pmoles;
++++++: ≤3.125 pmoles.
'−' means that no lysis was observed at the highest amount tested (100 pmoles).

Example 6

Control of Systemic MRSA Infection in a Murine Model

Expression and purification of recombinant, C-terminally 6×His-tagged phage endolysins were performed essentially as previously described (Donovan and Foster-Frey, supra), with the following modifications: Induced *E. coli* cultures were harvested, resuspended in 10 mL of lysis buffer (50 mM $NaH_2PO_4$, 300 mM NaCl, 10 mM imidazole, 30% glycerol, pH 8.0) per 1 L culture, and sonicated on ice for 5 min (1 s pulses separated by 1 s rests). After removal of debris by centrifugation (9000×g for 30 min), 6×His-tagged proteins were purified from the cleared supernatant by immobilized metal ion affinity chromatography, using nickel-NTA Superflow resin (QIAGEN, Valencia, Calif.). Purification columns were washed with 25 column volumes (CV) of lysis buffer supplemented with 0.1% Triton X-114 for removal of endotoxins (Reichelt et al. 2006. *Prot. Express. Purif.* 46:483-488), 40 CV of lysis buffer, and 15 CV of wash buffer (50 mM $NaH_2PO_4$, 300 mM NaCl, 20 mM imidazole, 30% glycerol, pH 8.0). Target proteins were eluted with elution buffer (50 mM $NaH_2PO_4$, 300 mM NaCl, 250 mM imidazole, 30% glycerol, pH 8.0) in 500 µl fractions. Fractions with high protein concentrations were combined and dialyzed against Dialysis Buffer (50 mM $NaH_2PO_4$, 300 mM NaCl, 10% glycerol, pH 7.5). Protein concentrations were measured spectrophotometrically using a NanoDrop ND-1000 (Nano-Drop Technologies, Wilmington, Del.), and purity was determined via sodium dodecyl sulfate-polyacrylamide gel electrophoresis (SDS-PAGE). Endotoxin concentrations were determined using a Limulus Amoebocyte Lysate (LAL) assay (Lonza, Walkersville, Md.). Endolysin activity was assayed using the plate lysis method essentially as described earlier (Becker et al. 2009b, supra).

Four to six week old female Balb/c mice (weight range 22 g to 24 g, Harlan Laboratories) were used in biosafety level 2 facilities in accordance with IACUC regulations. Briefly, methicillin-resistant *Staphylococcus aureus* (MRSA) strain NRS382, acquired from NARSA (Network on Antimicrobial Resistance in *Staphylococcus aureus*, Chantilly, Va.), was grown at 37° C. overnight in Brain Heart Infusion (BHI) medium (Becton, Dickinson and Company, Sparks, Md.). The culture was then diluted 1:100 and grown to mid-log phase ($OD_{600nm}$=0.3-0.4), centrifuged and resuspended in BHI supplemented with 5% mucin (Sigma-Aldrich St Louis, Mo., USA) for the mouse experiment. Mucin functions as immunosuppressant and allows reduction of the bacterial inoculum concentration required to achieve an $LD_{90}$ after 48 hours. Approximately $4×10^7$ CFU bacteria in suspension (in a volume of 0.2 ml) were injected intraperitoneally (I.P.). Actual inoculum titers were derived from plating serial dilutions of each inoculum on BHI agar plates.

Figure 5:
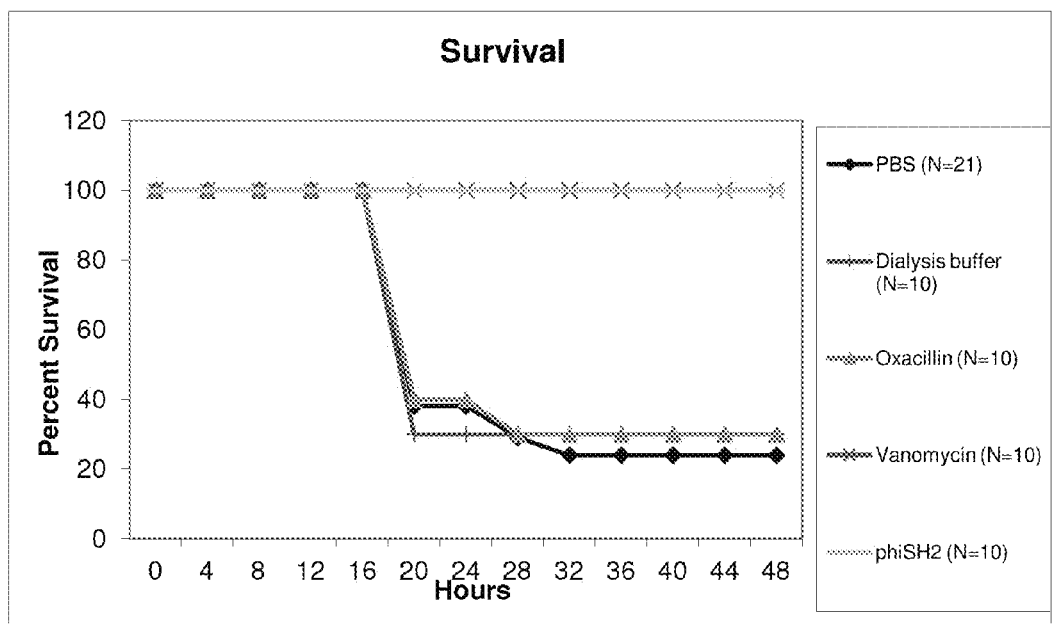
FIG. 5 depicts survival of mice infected intraperitoneally with $4\times10^7$ CFU of the MRSA strain NRS382 (NARSA) and treated 30 min post infection with 200 µg of phiSH2 full length endolysin by intraperitoneal injection. As controls, the buffers PBS and Dialysis Buffer (200 µl/mouse), and the antibiotics Vancomycin (375 µg/mouse) and Oxacillin (1250 µg/mouse) were used. Antibiotics were administered subcutaneously.

To determine the in vivo efficacy of φSH2 endolysin, 30 minutes post infection, infected mice were divided into several groups (ten mice in each group) and were I.P. injected with φSH2 endolysin (SEQ ID NO:2) in Dialysis Buffer (200 µg/mouse), or phosphate-buffered saline (PBS) or Dialysis Buffer as controls (0.2 ml/mouse). The antibiotics Vancomycin and Oxacillin (Sigma-Aldrich, St Louis, Mo., USA), prepared in distilled $H_2O$, were used as additional controls. Antibiotics were administrated subcutaneously (Vancomycin: 375 µg/mouse; Oxacillin: 1250 µg/mouse) 30 minutes post infection (FIG. 5 and Table 3). The survival rate for each experimental group was monitored every 4 hours up to 48 hours post infection. The data were statistically analyzed by Kaplan Meier Survival curves.

TABLE 3

In vivo Efficacy of ΦSH2 Endolysin, Oxacillin and Vancomycin.

| | % Survival | | | | |
|---|---|---|---|---|---|
| Hours | PBS | Dialysis Buffer | Oxacillin* | Vancomycin* | ΦSH2 Endolysin* |
| 0 | 100 | 100 | 100 | 100 | 100 |
| 4 | 100 | 100 | 100 | 100 | 100 |
| 8 | 100 | 100 | 100 | 100 | 100 |
| 12 | 100 | 100 | 100 | 100 | 100 |
| 16 | 100 | 100 | 100 | 100 | 100 |

TABLE 3-continued

In vivo Efficacy of ΦSH2 Endolysin, Oxacillin and Vancomycin.

| | | % Survival | | | |
|---|---|---|---|---|---|
| Hours | PBS | Dialysis Buffer | Oxacillin* | Vancomycin* | ΦSH2 Endolysin* |
| 20 | 38 | 30 | 40 | 100 | 100 |
| 24 | 38 | 30 | 40 | 100 | 100 |
| 28 | 29 | 30 | 30 | 100 | 100 |
| 32 | 24 | 30 | 30 | 100 | 100 |
| 36 | 24 | 30 | 30 | 100 | 100 |
| 40 | 24 | 30 | 30 | 100 | 100 |
| 44 | 24 | 30 | 30 | 100 | 100 |
| 48 | 24 | 30 | 30 | 100 | 100 |

*N = 10

Endolysin φSH2 protects mice from MRSA-induced bacteremia. The percentage of mice surviving after intraperitoneal injection of MRSA was monitored for 48 hours. For mice treated with PBS, Dialysis Buffer, or Oxacillin, the survival rate dropped from 100% to less than 40% after 16 to 20 hours, and reached approximately 20% at the end of the experiment (FIG. 5, Table 3). In contrast, 100% of the mice treated with either Vancomycin or the φSH2 endolysin, survived until 48 hours post infection.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. An isolated or recombinant cDNA encoding an antimicrobial φSH2 endolysin-derived peptidoglycan hydrolase molecule having specificity and exolytic activity for the peptidoglycan cell wall of untreated *Staphylococcus aureus* and coagulase negative staphylococci (CNS), said CNS comprising *S. chronogenes, S. epidermis, S. hyicus, S. simulans, S. wameri*, and *S. xylocus* wherein said cDNA encodes a truncated endolysin-derived peptidoglycan hydrolase molecule having the sequence of SEQ ID NO:4, SEQ ID NO:16 or SEQ ID NO:24.

2. The cDNA of claim 1 having the sequence of SEQ ID NO:3, SEQ ID NO:15 or SEQ ID NO:23, respectively.

3. A recombinant construct comprising the cDNA of claim 1, wherein said cDNA is in operable linkage to a promoter that drives expression in a host cell.

4. A cloning vector comprising the recombinant construct of claim 3.

5. An expression vector comprising the recombinant construct of claim 3.

6. A process for transforming a host cell, comprising stably integrating the cDNA in claim 1 or the construct of claim 3 into the host cell.

7. An isolated host cell transformed with the cDNA according to claim 1.

8. An isolated host cell transformed with the recombinant construct according to claim 3.

9. A method of making a recombinant peptidoglycan hydrolase protein, said method comprising steps:
  a. inducing into an isolated host cell the cDNA of claim 1 or the recombinant construct of claim 3 encoding the truncated endolysin-derived peptidoglycan hydrolase molecule;
  b. culturing said cell under conditions suitable for expression of said protein;
  c. recovering the protein so expressed.

* * * * *

SEQUENCE LISTING

<160> NUMBER OF SEQ ID NOS: 38

<210> SEQ ID NO 1
<211> LENGTH: 1506
<212> TYPE: DNA
<213> ORGANISM: Bacteriophage Phi SH2

<400> SEQUENCE: 1

```
atgaaaacac aagcagagat taataaacgg ttagacgctt atagaaaagg cacagttgat      60
agtccatata gagttaaagt ttggacgagt tacgataacc gtttctatcc aatggaaccg     120
ggctgtatcg atgtagacaa aagtttccac gctcaatgtg ctgatttaac aatcgactat     180
attttgtggc ttactgataa tgagtttaga attagaggga atgcaaaaga tgcaataaac     240
cctaaaaaga ataagttgcc agaaggatgg aaaattgttt taaacagacc ttcaacagtc     300
cctagaaaag gttggatagc tgttttttact gatggaactt attgggaata cggtcacatt     360
ggtatggttt atgatggtgg taatacaagt cgttttcaaa ttttagagca aaactggaat     420
ggttgggcta ataagaaacc tagcctacgt tgggataatt attatggttt aactcatttt     480
attgttccac cagtagctaa agaaaataaa gctgtttcat caagcaaaca acaagcacct     540
aaacaaaaag ttaaaaaagc atctactaaa aaagcattac ctaaaatcac taaacacatc     600
actggttata atatggataa acgaggttac aaccctaaag gtgtagtttt acacaatgat     660
gcaggaggta tgaactataa acaatattac aacaacttag ttaatgctaa ctatgaccgt     720
ttagcgcgtg gtatcgcaca tgcttatgtt gatagaacag gcatttggga agcaatagac     780
gaaagtcgta tagcgtggca tgtagcagat ggcactcgac ctggaagtgg taatcatgat     840
ttctacggta tcgaagtgaa tcaatcatta cgtgcaagtg ataaagaatt cttagagaat     900
gaacaagctg ttttccaatt cgcagcagaa aaactaaaaa agtggggatt accagcaaac     960
agaaataccg ttcgtttgca taatgaattt agtcagacaa gttgtccaca cagaagtatg    1020
gtgcttcata ctggtttaga tccgttgtat cactcaatta ctgaacatgc acgactaaaa    1080
ttaaaagatt acttcattaa acaaattaga gcgtatatgg atggtaagaa accaacttct    1140
aaagtagttg taagcaaacc gggtagtgct tctacaccag ctacacgtaa agacgctaac    1200
ggttatagag aaaatccgca tgggacgtta tataagaag aacacgcaac atttacagca    1260
aatgctaaca tcatcactcg ttacgttggg cctttcacaa atatgcctca agctggcatt    1320
ttaaaagctg gtcaaacgat tatatatgat gaagtaatga acaagacgg ttatatttgg    1380
```

```
gtaggttaca ctgcatataa tggcaaacgt gtttatttac cagttagaaa atggaacaga    1440
gaaacagata gtgtaggtaa attatgggga gtaatcagtc tcgagcacca ccaccaccac    1500
cactga                                                                1506
```

<210> SEQ ID NO 2
<211> LENGTH: 501
<212> TYPE: PRT
<213> ORGANISM: Bacteriophage Phi SH2

<400> SEQUENCE: 2

```
Met Lys Thr Gln Ala Glu Ile Asn Lys Arg Leu Asp Ala Tyr Arg Lys
1               5                   10                  15

Gly Thr Val Asp Ser Pro Tyr Arg Val Lys Val Trp Thr Ser Tyr Asp
            20                  25                  30

Asn Arg Phe Tyr Pro Met Glu Pro Gly Cys Ile Asp Val Asp Lys Ser
        35                  40                  45

Phe His Ala Gln Cys Ala Asp Leu Thr Ile Asp Tyr Ile Leu Trp Leu
    50                  55                  60

Thr Asp Asn Glu Phe Arg Ile Arg Gly Asn Ala Lys Asp Ala Ile Asn
65                  70                  75                  80

Pro Lys Lys Asn Lys Leu Pro Glu Gly Trp Lys Ile Val Leu Asn Arg
                85                  90                  95

Pro Ser Thr Val Pro Arg Lys Gly Trp Ile Ala Val Phe Thr Asp Gly
            100                 105                 110

Thr Tyr Trp Glu Tyr Gly His Ile Gly Met Val Tyr Asp Gly Gly Asn
        115                 120                 125

Thr Ser Arg Phe Gln Ile Leu Glu Gln Asn Trp Asn Gly Trp Ala Asn
    130                 135                 140

Lys Lys Pro Ser Leu Arg Trp Asp Asn Tyr Tyr Gly Leu Thr His Phe
145                 150                 155                 160

Ile Val Pro Pro Val Ala Lys Glu Asn Lys Ala Val Ser Ser Ser Lys
                165                 170                 175

Gln Gln Ala Pro Lys Gln Lys Val Lys Lys Ala Ser Thr Lys Lys Ala
            180                 185                 190

Leu Pro Lys Ile Thr Lys His Ile Thr Gly Tyr Asn Met Asp Lys Arg
        195                 200                 205

Gly Tyr Asn Pro Lys Gly Val Val Leu His Asn Asp Ala Gly Gly Met
    210                 215                 220

Asn Tyr Lys Gln Tyr Tyr Asn Asn Leu Val Asn Ala Asn Tyr Asp Arg
225                 230                 235                 240

Leu Ala Arg Gly Ile Ala His Ala Tyr Val Asp Arg Thr Gly Ile Trp
                245                 250                 255

Glu Ala Ile Asp Glu Ser Arg Ile Ala Trp His Val Ala Asp Gly Thr
            260                 265                 270

Arg Pro Gly Ser Gly Asn His Asp Phe Tyr Gly Ile Glu Val Asn Gln
        275                 280                 285

Ser Leu Arg Ala Ser Asp Lys Glu Phe Leu Glu Asn Glu Gln Ala Val
    290                 295                 300

Phe Gln Phe Ala Ala Glu Lys Leu Lys Lys Trp Gly Leu Pro Ala Asn
305                 310                 315                 320

Arg Asn Thr Val Arg Leu His Asn Glu Phe Ser Gln Thr Ser Cys Pro
                325                 330                 335

His Arg Ser Met Val Leu His Thr Gly Leu Asp Pro Leu Tyr His Ser
```

```
            340                 345                 350
Ile Thr Glu His Ala Arg Leu Lys Leu Lys Asp Tyr Phe Ile Lys Gln
            355                 360                 365

Ile Arg Ala Tyr Met Asp Gly Lys Lys Pro Thr Ser Lys Val Val Val
        370                 375                 380

Ser Lys Pro Gly Ser Ala Ser Thr Pro Ala Thr Arg Lys Asp Ala Asn
385                 390                 395                 400

Gly Tyr Arg Glu Asn Pro His Gly Thr Leu Tyr Lys Glu His Ala
                405                 410                 415

Thr Phe Thr Ala Asn Ala Asn Ile Ile Thr Arg Tyr Val Gly Pro Phe
        420                 425                 430

Thr Asn Met Pro Gln Ala Gly Ile Leu Lys Ala Gly Gln Thr Ile Ile
            435                 440                 445

Tyr Asp Glu Val Met Lys Gln Asp Gly Tyr Ile Trp Val Gly Tyr Thr
        450                 455                 460

Ala Tyr Asn Gly Lys Arg Val Tyr Leu Pro Val Arg Lys Trp Asn Arg
465                 470                 475                 480

Glu Thr Asp Ser Val Gly Lys Leu Trp Gly Val Ile Ser Leu Glu His
                485                 490                 495

His His His His His
            500

<210> SEQ ID NO 3
<211> LENGTH: 525
<212> TYPE: DNA
<213> ORGANISM: Bacteriophage Phi SH2

<400> SEQUENCE: 3
atgaaaacac aagcagagat taataaacgg ttagacgctt atagaaaagg cacagttgat      60
agtccatata gagttaaagt ttggacgagt tacgataacc gtttctatcc aatggaaccg     120
ggctgtatcg atgtagacaa aagttttcca gctcaatgtg ctgatttaac aatcgactat     180
attttgtggc ttactgataa tgagtttaga attagaggga atgcaaaaga tgcaataaac     240
cctaaaaaga taagttgcc agaaggatgg aaaattgttt taaacagacc ttcaacagtc     300
cctagaaaag gttggatagc tgtttttact gatggaactt attgggaata cggtcacatt     360
ggtatggttt atgatggtgg taatacaagt cgttttcaaa ttttagagca aaactggaat     420
ggttgggcta ataagaaacc tagcctacgt tgggataatt attatggttt aactcatttt     480
attgttccac cagtagctct cgagcaccac caccaccacc actga                     525

<210> SEQ ID NO 4
<211> LENGTH: 174
<212> TYPE: PRT
<213> ORGANISM: Bacteriophage Phi SH2

<400> SEQUENCE: 4

Met Lys Thr Gln Ala Glu Ile Asn Lys Arg Leu Asp Ala Tyr Arg Lys
1               5                   10                  15

Gly Thr Val Asp Ser Pro Tyr Arg Val Lys Val Trp Thr Ser Tyr Asp
            20                  25                  30

Asn Arg Phe Tyr Pro Met Glu Pro Gly Cys Ile Asp Val Asp Lys Ser
        35                  40                  45

Phe His Ala Gln Cys Ala Asp Leu Thr Ile Asp Tyr Ile Leu Trp Leu
    50                  55                  60

Thr Asp Asn Glu Phe Arg Ile Arg Gly Asn Ala Lys Asp Ala Ile Asn
```

Pro Lys Lys Asn Lys Leu Pro Glu Gly Trp Lys Ile Val Leu Asn Arg
            85                  90                  95

Pro Ser Thr Val Pro Arg Lys Gly Trp Ile Ala Val Phe Thr Asp Gly
            100                 105                 110

Thr Tyr Trp Glu Tyr Gly His Ile Gly Met Val Tyr Asp Gly Gly Asn
            115                 120                 125

Thr Ser Arg Phe Gln Ile Leu Glu Gln Asn Trp Asn Gly Trp Ala Asn
            130                 135                 140

Lys Lys Pro Ser Leu Arg Trp Asp Asn Tyr Tyr Gly Leu Thr His Phe
145                 150                 155                 160

Ile Val Pro Pro Val Ala Leu Glu His His His His His His
            165                 170

<210> SEQ ID NO 5
<211> LENGTH: 657
<212> TYPE: DNA
<213> ORGANISM: Bacteriophage Phi SH2

<400> SEQUENCE: 5
atgaaaacac aagcagagat taataaacgg ttagacgctt atagaaaagg cacagttgat      60
agtccatata gagttaaagt ttggacgagt tacgataacc gtttctatcc aatggaaccg     120
ggctgtatcg atgtagacaa agtttccac gctcaatgtg ctgatttaac aatcgactat     180
attttgtggc ttactgataa tgagtttaga attagaggga atgcaaaaga tgcaataaac     240
cctaaaaaga taagttgcc agaaggatgg aaaattgttt taaacagacc ttcaacagtc     300
cctagaaaag gttggatagc tgttttact gatggaactt attgggaata cggtcacatt     360
ggtatggttt atgatggtgg taatacaagt cgttttcaaa ttttagagca aaactggaat     420
ggttgggcta ataagaaacc tagcctacgt tgggataatt attatggttt aactcatttt     480
attgttccac cagtagctaa agaaataaa gctgtttcat caagcaaaca acaagcaccac     540
aaacaaaaag ttaaaaaagc atctactaaa aaagcattac ctaaaatcac taaacacatc     600
actggtttata atatgagataa acgaggttac ctcgagcacc accaccacca ccactga     657

<210> SEQ ID NO 6
<211> LENGTH: 218
<212> TYPE: PRT
<213> ORGANISM: Bacteriophage Phi SH2

<400> SEQUENCE: 6

Met Lys Thr Gln Ala Glu Ile Asn Lys Arg Leu Asp Ala Tyr Arg Lys
1               5                   10                  15

Gly Thr Val Asp Ser Pro Tyr Arg Val Lys Val Trp Thr Ser Tyr Asp
            20                  25                  30

Asn Arg Phe Tyr Pro Met Glu Pro Gly Cys Ile Asp Val Asp Lys Ser
            35                  40                  45

Phe His Ala Gln Cys Ala Asp Leu Thr Ile Asp Tyr Ile Leu Trp Leu
            50                  55                  60

Thr Asp Asn Glu Phe Arg Ile Arg Gly Asn Ala Lys Asp Ala Ile Asn
65                  70                  75                  80

Pro Lys Lys Asn Lys Leu Pro Glu Gly Trp Lys Ile Val Leu Asn Arg
            85                  90                  95

Pro Ser Thr Val Pro Arg Lys Gly Trp Ile Ala Val Phe Thr Asp Gly
            100                 105                 110

Thr Tyr Trp Glu Tyr Gly His Ile Gly Met Val Tyr Asp Gly Gly Asn
            115                 120                 125

Thr Ser Arg Phe Gln Ile Leu Glu Gln Asn Trp Asn Gly Trp Ala Asn
        130                 135                 140

Lys Lys Pro Ser Leu Arg Trp Asp Asn Tyr Tyr Gly Leu Thr His Phe
145                 150                 155                 160

Ile Val Pro Pro Val Ala Lys Glu Asn Lys Ala Val Ser Ser Ser Lys
                165                 170                 175

Gln Gln Ala Pro Lys Gln Lys Val Lys Lys Ala Ser Thr Lys Lys Ala
            180                 185                 190

Leu Pro Lys Ile Thr Lys His Ile Thr Gly Tyr Asn Met Asp Lys Arg
        195                 200                 205

Gly Tyr Leu Glu His His His His His His
    210                 215

<210> SEQ ID NO 7
<211> LENGTH: 762
<212> TYPE: DNA
<213> ORGANISM: Bacteriophage Phi SH2

<400> SEQUENCE: 7
atgaaaacac aagcagagat taataaacgg ttagacgctt atagaaaagg cacagttgat      60
agtccatata gagttaaagt ttggacgagt tacgataacc gtttctatcc aatggaaccg     120
ggctgtatcg atgtagacaa agtttccac gctcaatgtg ctgatttaac aatcgactat      180
attttgtggc ttactgataa tgagtttaga attagaggga atgcaaaaga tgcaataaac     240
cctaaaaaga ataagttgcc agaaggatgg aaaattgttt aaacagacc ttcaacagtc      300 cctagaaaag gttggatagc tgtttttact gatggaactt attgggaata cggtcacatt     360
ggtatggttt atgatggtgg taatacaagt cgttttcaaa ttttagagca aaactggaat     420
ggttgggcta ataagaaacc tagcctacgt tgggataatt attatggttt aactcatttt     480
attgttccac cagtagctaa agaaaataaa gctgtttcat caagcaaaca acaagcacct     540
aaacaaaaag ttaaaaaagc atctactaaa aaagcattac ctaaaatcac taaacacatc     600
actggttata tatggataaa cgaggttac aaccctaaag gtgtagtttt acacaatgat      660
gcaggaggta tgaactataa acaatattac aacaacttag ttaatgctaa ctatgaccgt     720
ttagcgcgtg gtatcctcga gcaccaccac caccaccact ga                        762

<210> SEQ ID NO 8
<211> LENGTH: 253
<212> TYPE: PRT
<213> ORGANISM: Bacteriophage Phi SH2

<400> SEQUENCE: 8

Met Lys Thr Gln Ala Glu Ile Asn Lys Arg Leu Asp Ala Tyr Arg Lys
1               5                   10                  15

Gly Thr Val Asp Ser Pro Tyr Arg Val Lys Val Trp Thr Ser Tyr Asp
            20                  25                  30

Asn Arg Phe Tyr Pro Met Glu Pro Gly Cys Ile Asp Val Asp Lys Ser
        35                  40                  45

Phe His Ala Gln Cys Ala Asp Leu Thr Ile Asp Tyr Ile Leu Trp Leu
    50                  55                  60

Thr Asp Asn Glu Phe Arg Ile Arg Gly Asn Ala Lys Asp Ala Ile Asn
65                  70                  75                  80

Pro Lys Lys Asn Lys Leu Pro Glu Gly Trp Lys Ile Val Leu Asn Arg

|   |   |   | 85 |   |   |   | 90 |   |   |   | 95 |   |   |
|---|---|---|---|---|---|---|---|---|---|---|---|---|---|

Pro Ser Thr Val Pro Arg Lys Gly Trp Ile Ala Val Phe Thr Asp Gly
              100              105              110

Thr Tyr Trp Glu Tyr Gly His Ile Gly Met Val Tyr Asp Gly Gly Asn
     115               120              125

Thr Ser Arg Phe Gln Ile Leu Glu Gln Asn Trp Asn Gly Trp Ala Asn
     130               135              140

Lys Lys Pro Ser Leu Arg Trp Asp Asn Tyr Tyr Gly Leu Thr His Phe
145              150              155              160

Ile Val Pro Val Ala Lys Glu Asn Lys Ala Val Ser Ser Lys
              165              170              175

Gln Gln Ala Pro Lys Gln Lys Val Lys Lys Ala Ser Thr Lys Lys Ala
            180              185              190

Leu Pro Lys Ile Thr Lys His Ile Thr Gly Tyr Asn Met Asp Lys Arg
              195              200              205

Gly Tyr Asn Pro Lys Gly Val Val Leu His Asn Asp Ala Gly Gly Met
     210               215              220

Asn Tyr Lys Gln Tyr Tyr Asn Asn Leu Val Asn Ala Asn Tyr Asp Arg
225              230              235              240

Leu Ala Arg Gly Ile Leu Glu His His His His His His
              245              250

<210> SEQ ID NO 9
<211> LENGTH: 888
<212> TYPE: DNA
<213> ORGANISM: Bacteriophage Phi SH2

<400> SEQUENCE: 9

```
atgaaaacac aagcagagat taataaacgg ttagacgctt atagaaaagg cacagttgat    60
agtccatata gagttaaagt ttggacgagt tacgataacc gtttctatcc aatggaaccg   120
ggctgtatcg atgtagacaa aagtttccac gctcaatgtg ctgatttaac aatcgactat   180
attttgtggc ttactgataa tgagtttaga attagaggga atgcaaaaga tgcaataaac   240
cctaaaaaga ataagttgcc agaaggatgg aaaattgttt aaacagacc ttcaacagtc   300
cctagaaaag gttggatagc tgttttact gatggaactt attgggaata cggtcacatt   360
ggtatggttt atgatggtgg taatacaagt cgttttcaaa ttttagagca aaactgaat   420
ggttgggcta ataagaaacc tagcctacgt tgggataatt attatggttt aactcatttt   480
attgttccac cagtagctaa agaaaataaa gctgtttcat caagcaaaca acaagcacct   540
aaacaaaaag ttaaaaaagc atctactaaa aaagcattac ctaaaatcac taaacacatc   600
actggttata atatggataa acgaggttac aaccctaaag gtgtagtttt acacaatgat   660
gcaggaggta tgaactataa acaatattac aacaacttag ttaatgctaa ctatgaccgt   720
ttagcgcgtg gtatcgcaca tgcttatgtt gatagaacag gcatttggga agcaatagac   780
gaaagtcgta tagcgtggca tgtagcagat ggcactcgac ctggaagtgg taatcatgat   840
ttctacggta tcgaagtgaa tctcgagcac caccaccacc accactga               888
```

<210> SEQ ID NO 10
<211> LENGTH: 295
<212> TYPE: PRT
<213> ORGANISM: Bacteriophage Phi SH2

<400> SEQUENCE: 10

Met Lys Thr Gln Ala Glu Ile Asn Lys Arg Leu Asp Ala Tyr Arg Lys

```
              1               5                  10                 15
            Gly Thr Val Asp Ser Pro Tyr Arg Val Lys Val Trp Thr Ser Tyr Asp
                            20                 25                 30
            Asn Arg Phe Tyr Pro Met Glu Pro Gly Cys Ile Asp Val Asp Lys Ser
                            35                 40                 45
            Phe His Ala Gln Cys Ala Asp Leu Thr Ile Asp Tyr Ile Leu Trp Leu
             50                 55                 60
            Thr Asp Asn Glu Phe Arg Ile Arg Gly Asn Ala Lys Asp Ala Ile Asn
             65                 70                 75                 80
            Pro Lys Lys Asn Lys Leu Pro Glu Gly Trp Lys Ile Val Leu Asn Arg
                            85                 90                 95
            Pro Ser Thr Val Pro Arg Lys Gly Trp Ile Ala Val Phe Thr Asp Gly
                           100                105                110
            Thr Tyr Trp Glu Tyr Gly His Ile Gly Met Val Tyr Asp Gly Gly Asn
                           115                120                125
            Thr Ser Arg Phe Gln Ile Leu Glu Gln Asn Trp Asn Gly Trp Ala Asn
                           130                135                140
            Lys Lys Pro Ser Leu Arg Trp Asp Asn Tyr Tyr Gly Leu Thr His Phe
            145                150                155                160
            Ile Val Pro Pro Val Ala Lys Glu Asn Lys Ala Val Ser Ser Ser Lys
                           165                170                175
            Gln Gln Ala Pro Lys Gln Lys Val Lys Lys Ala Ser Thr Lys Lys Ala
                           180                185                190
            Leu Pro Lys Ile Thr Lys His Ile Thr Gly Tyr Asn Met Asp Lys Arg
                           195                200                205
            Gly Tyr Asn Pro Lys Gly Val Val Leu His Asn Asp Ala Gly Gly Met
                           210                215                220
            Asn Tyr Lys Gln Tyr Tyr Asn Asn Leu Val Asn Ala Asn Tyr Asp Arg
            225                230                235                240
            Leu Ala Arg Gly Ile Ala His Ala Tyr Val Asp Arg Thr Gly Ile Trp
                           245                250                255
            Glu Ala Ile Asp Glu Ser Arg Ile Ala Trp His Val Ala Asp Gly Thr
                           260                265                270
            Arg Pro Gly Ser Gly Asn His Asp Phe Tyr Gly Ile Glu Val Asn Leu
                           275                280                285
            Glu His His His His His His
                           290                295

<210> SEQ ID NO 11
<211> LENGTH: 990
<212> TYPE: DNA
<213> ORGANISM: Bacteriophage Phi SH2

<400> SEQUENCE: 11
atgaaaacac aagcagagat taataaacgg ttagacgctt atagaaaagg cacagttgat      60
agtccatata gagttaaagt ttggacgagt tacgataacc gtttctatcc aatggaaccg     120
ggctgtatcg atgtagacaa aagttttcca cgctcaatgtg ctgatttaac aatcgactat     180
attttgtggc ttactgataa tgagtttaga attagaggga tgcaaaaga tgcaataaac     240 cctaaaaaga ataagttgcc agaaggatgg aaaattgttt taaacagacc ttcaacagtc     300
cctagaaaag gttggatagc tgttttttact gatggaactt attgggaata cggtcacatt     360
ggtatggttt atgatggtgg taatacaagt cgttttcaaa ttttagagca aaactggaat     420
ggttgggcta ataagaaacc tagcctacgt tgggataatt attatggttt aactcatttt     480
```

```
attgttccac cagtagctct cgaggtgctt catactggtt tagatccgtt gtatcactca    540
attactgaac atgcacgact aaaattaaaa gattacttca ttaaacaaat tagagcgtat    600
atggatggta agaaaccaac ttctaaagta gttgtaagca aaccgggtag tgcttctaca    660
ccagctacac gtaaagacgc taacggttat agagaaaatc cgcatgggac gttatataaa    720
gaagaacacg caacatttac agcaaatgct aacatcatca ctcgttacgt tgggcctttc    780
acaaatatgc ctcaagctgg cattttaaaa gctggtcaaa cgattatata tgatgaagta    840
atgaaacaag acggttatat ttgggtaggt tacactgcat ataatggcaa acgtgtttat    900
ttaccagtta gaaaatggaa cagagaaaca gatagtgtag gtaaattatg gggagtaatc    960
agtctcgagc accaccacca ccaccactga    990
```

<210> SEQ ID NO 12
<211> LENGTH: 329
<212> TYPE: PRT
<213> ORGANISM: Bacteriophage Phi SH2

<400> SEQUENCE: 12

```
Met Lys Thr Gln Ala Glu Ile Asn Lys Arg Leu Asp Ala Tyr Arg Lys
1               5                   10                  15

Gly Thr Val Asp Ser Pro Tyr Arg Val Lys Val Trp Thr Ser Tyr Asp
            20                  25                  30

Asn Arg Phe Tyr Pro Met Glu Pro Gly Cys Ile Asp Val Asp Lys Ser
        35                  40                  45

Phe His Ala Gln Cys Ala Asp Leu Thr Ile Asp Tyr Ile Leu Trp Leu
    50                  55                  60

Thr Asp Asn Glu Phe Arg Ile Arg Gly Asn Ala Lys Asp Ala Ile Asn
65                  70                  75                  80

Pro Lys Lys Asn Lys Leu Pro Glu Gly Trp Lys Ile Val Leu Asn Arg
                85                  90                  95

Pro Ser Thr Val Pro Arg Lys Gly Trp Ile Ala Val Phe Thr Asp Gly
            100                 105                 110

Thr Tyr Trp Glu Tyr Gly His Ile Gly Met Val Tyr Asp Gly Gly Asn
        115                 120                 125

Thr Ser Arg Phe Gln Ile Leu Glu Gln Asn Trp Asn Gly Trp Ala Asn
    130                 135                 140

Lys Lys Pro Ser Leu Arg Trp Asp Asn Tyr Tyr Gly Leu Thr His Phe
145                 150                 155                 160

Ile Val Pro Pro Val Ala Leu Glu Val Leu His Thr Gly Leu Asp Pro
                165                 170                 175

Leu Tyr His Ser Ile Thr Glu His Ala Arg Leu Lys Leu Lys Asp Tyr
            180                 185                 190

Phe Ile Lys Gln Ile Arg Ala Tyr Met Asp Gly Lys Lys Pro Thr Ser
        195                 200                 205

Lys Val Val Ser Lys Pro Gly Ser Ala Ser Thr Pro Ala Thr Arg
    210                 215                 220

Lys Asp Ala Asn Gly Tyr Arg Glu Asn Pro His Gly Thr Leu Tyr Lys
225                 230                 235                 240

Glu Glu His Ala Thr Phe Thr Ala Asn Ala Asn Ile Ile Thr Arg Tyr
                245                 250                 255

Val Gly Pro Phe Thr Asn Met Pro Gln Ala Gly Ile Leu Lys Ala Gly
            260                 265                 270

Gln Thr Ile Ile Tyr Asp Glu Val Met Lys Gln Asp Gly Tyr Ile Trp
```

```
                275                 280                 285
Val Gly Tyr Thr Ala Tyr Asn Gly Lys Arg Val Tyr Leu Pro Val Arg
            290                 295                 300

Lys Trp Asn Arg Glu Thr Asp Ser Val Gly Lys Leu Trp Gly Val Ile
305                 310                 315                 320

Ser Leu Glu His His His His His His
                325
```

<210> SEQ ID NO 13
<211> LENGTH: 1209
<212> TYPE: DNA
<213> ORGANISM: Bacteriophage Phi SH2

<400> SEQUENCE: 13

```
atgaaaacac aagcagagat taataaacgg ttagacgctt atagaaaagg cacagttgat      60
agtccatata gagttaaagt ttggacgagt tacgataacc gtttctatcc aatggaaccg     120
ggctgtatcg atgtagacaa agtttccac gctcaatgtg ctgatttaac aatcgactat      180
attttgtggc ttactgataa tgagtttaga attagaggga atgcaaaaga tgcaataaac     240
cctaaaaaga ataagttgcc agaaggatgg aaaattgttt aaacagacc ttcaacagtc      300
cctagaaaag gttggatagc tgtttttact gatggaactt attgggaata cggtcacatt     360
ggtatggttt atgatggtgg taatacaagt cgttttcaaa ttttagagca aaactggaat     420
ggttgggcta ataagaaacc tagcctacgt tgggataatt attatggttt aactcatttt     480
attgttccac cagtagctaa agaaaataaa gctgtttcat caagcaaaca acaagcacct     540
aaacaaaaag ttaaaaaagc atctactaaa aaagcattac ctaaaatcac taaacacatc     600
actggttata atatggataa acgaggttac aaccctaaag gtgtagttt acacaatgat      660
gcaggaggta tgaactataa acaatattac aacaacttag ttaatgctaa ctatgaccgt     720
ttagcgcgtg gtatcctcga ggatccgttg tatcactcaa ttactgaaca tgcacgacta     780
aaattaaaag attacttcat taaacaaatt agagcgtata tggatggtaa gaaaccaact     840
tctaaagtag ttgtaagcaa accgggtagt gcttctacac cagctacacg taaagacgct     900
aacggttata gagaaaatcc gcatgggacg ttatataaag aagaacacgc aacatttaca     960
gcaaatgcta acatcatcac tcgttacgtt gggcctttca caaatatgcc tcaagctggc    1020
attttaaaag ctggtcaaac gattatatat gatgaagtaa tgaaacaaga cggttatatt    1080
tgggtaggtt acactgcata taatggcaaa cgtgtttatt taccagttag aaaatggaac    1140
agagaaacag atagtgtagg taaattatgg ggagtaatca gtctcgagca ccaccaccac    1200
caccactga                                                            1209
```

<210> SEQ ID NO 14
<211> LENGTH: 402
<212> TYPE: PRT
<213> ORGANISM: Bacteriophage Phi SH2

<400> SEQUENCE: 14

```
Met Lys Thr Gln Ala Glu Ile Asn Lys Arg Leu Asp Ala Tyr Arg Lys
1               5                   10                  15

Gly Thr Val Asp Ser Pro Tyr Arg Val Lys Val Trp Thr Ser Tyr Asp
            20                  25                  30

Asn Arg Phe Tyr Pro Met Glu Pro Gly Cys Ile Asp Val Asp Lys Ser
        35                  40                  45

Phe His Ala Gln Cys Ala Asp Leu Thr Ile Asp Tyr Ile Leu Trp Leu
```

```
                50                  55                  60
Thr Asp Asn Glu Phe Arg Ile Arg Gly Asn Ala Lys Asp Ala Ile Asn
 65                  70                  75                  80

Pro Lys Lys Asn Lys Leu Pro Glu Gly Trp Lys Ile Val Leu Asn Arg
                 85                  90                  95

Pro Ser Thr Val Pro Arg Lys Gly Trp Ile Ala Val Phe Thr Asp Gly
            100                 105                 110

Thr Tyr Trp Glu Tyr Gly His Ile Gly Met Val Tyr Asp Gly Gly Asn
        115                 120                 125

Thr Ser Arg Phe Gln Ile Leu Glu Gln Asn Trp Asn Gly Trp Ala Asn
    130                 135                 140

Lys Lys Pro Ser Leu Arg Trp Asp Asn Tyr Tyr Gly Leu Thr His Phe
145                 150                 155                 160

Ile Val Pro Pro Val Ala Lys Glu Asn Lys Ala Val Ser Ser Ser Lys
                165                 170                 175

Gln Gln Ala Pro Lys Gln Lys Val Lys Lys Ala Ser Thr Lys Lys Ala
            180                 185                 190

Leu Pro Lys Ile Thr Lys His Ile Thr Gly Tyr Asn Met Asp Lys Arg
        195                 200                 205

Gly Tyr Asn Pro Lys Gly Val Val Leu His Asn Asp Ala Gly Gly Met
    210                 215                 220

Asn Tyr Lys Gln Tyr Tyr Asn Asn Leu Val Asn Ala Asn Tyr Asp Arg
225                 230                 235                 240

Leu Ala Arg Gly Ile Leu Glu Asp Pro Leu Tyr His Ser Ile Thr Glu
                245                 250                 255

His Ala Arg Leu Lys Leu Lys Asp Tyr Phe Ile Lys Gln Ile Arg Ala
            260                 265                 270

Tyr Met Asp Gly Lys Lys Pro Thr Ser Lys Val Val Ser Lys Pro
        275                 280                 285

Gly Ser Ala Ser Thr Pro Ala Thr Arg Lys Asp Ala Asn Gly Tyr Arg
    290                 295                 300

Glu Asn Pro His Gly Thr Leu Tyr Lys Glu His Ala Thr Phe Thr
305                 310                 315                 320

Ala Asn Ala Asn Ile Ile Thr Arg Tyr Val Gly Pro Phe Thr Asn Met
                325                 330                 335

Pro Gln Ala Gly Ile Leu Lys Ala Gly Gln Thr Ile Ile Tyr Asp Glu
            340                 345                 350

Val Met Lys Gln Asp Gly Tyr Ile Trp Val Gly Tyr Thr Ala Tyr Asn
        355                 360                 365

Gly Lys Arg Val Tyr Leu Pro Val Arg Lys Trp Asn Arg Glu Thr Asp
    370                 375                 380

Ser Val Gly Lys Leu Trp Gly Val Ile Ser Leu Glu His His His His
385                 390                 395                 400

His His

<210> SEQ ID NO 15
<211> LENGTH: 1218
<212> TYPE: DNA
<213> ORGANISM: Bacteriophage Phi SH2

<400> SEQUENCE: 15
atgaaaacac aagcagagat taataaacgg ttagacgctt atagaaaagg cacagttgat    60
agtccatata gagttaaagt ttggacgagt tacgataacc gtttctatcc aatggaaccg   120
```

-continued

```
ggctgtatcg atgtagacaa aagtttccac gctcaatgtg ctgatttaac aatcgactat    180
attttgtggc ttactgataa tgagtttaga attagaggga atgcaaaaga tgcaataaac    240
cctaaaaaga ataagttgcc agaaggatgg aaaattgttt taaacagacc ttcaacagtc    300
cctagaaaag gttggatagc tgttttttact gatggaactt attgggaata cggtcacatt    360
ggtatggttt atgatggtgg taatacaagt cgttttcaaa ttttagagca aaactggaat    420
ggttgggcta ataagaaacc tagcctacgt tgggataatt attatggttt aactcatttt    480
attgttccac cagtagctaa agaaaataaa gctgtttcat caagcaaaca acaagcacct    540
aaacaaaaag ttaaaaaagc atctactaaa aaagcattac ctaaaatcac taaacacatc    600
actggttata atatggataa acgaggttac aaccctaaag gtgtagtttt acacaatgat    660
gcaggaggta tgaactataa acaatattac aacaacttag ttaatgctaa ctatgaccgt    720
ttagcgcgtg gtatcgcaca tgcttatgtt gatagaacag gcatttggga agcaatagac    780
gaaagtcgta tagcgtggca tgtagcagat ggcactcgac ctggaagtgg taatcatgat    840
ttctacggta tcgaagtgaa tcaatcatta cgtgcaagtg ataaagaatt cttagagaat    900
gaacaagctg ttttccaatt cgcagcagaa aaactaaaaa agtggggatt accagcaaac    960
agaaataccg ttcgtttgca taatgaattt agtcagacaa gttgtccaca cagaagtatg   1020
gtgcttcata ctggtttaga tccgttgtat cactcaatta ctgaacatgc acgactaaaa   1080
ttaaaagatt acttcattaa acaaattaga gcgtatatgg atggtaagaa accaacttct   1140
aaagtagttg taagcaaacc gggtagtgct tctacaccag ctacacgtaa actcgagcac   1200
caccaccacc accactga                                                 1218
```

<210> SEQ ID NO 16
<211> LENGTH: 405
<212> TYPE: PRT
<213> ORGANISM: Bacteriophage Phi SH2

<400> SEQUENCE: 16

```
Met Lys Thr Gln Ala Glu Ile Asn Lys Arg Leu Asp Ala Tyr Arg Lys
1               5                   10                  15

Gly Thr Val Asp Ser Pro Tyr Arg Val Lys Val Trp Thr Ser Tyr Asp
            20                  25                  30

Asn Arg Phe Tyr Pro Met Glu Pro Gly Cys Ile Asp Val Asp Lys Ser
        35                  40                  45

Phe His Ala Gln Cys Ala Asp Leu Thr Ile Asp Tyr Ile Leu Trp Leu
    50                  55                  60

Thr Asp Asn Glu Phe Arg Ile Arg Gly Asn Ala Lys Asp Ala Ile Asn
65                  70                  75                  80

Pro Lys Lys Asn Lys Leu Pro Glu Gly Trp Lys Ile Val Leu Asn Arg
                85                  90                  95

Pro Ser Thr Val Pro Arg Lys Gly Trp Ile Ala Val Phe Thr Asp Gly
            100                 105                 110

Thr Tyr Trp Glu Tyr Gly His Ile Gly Met Val Tyr Asp Gly Gly Asn
        115                 120                 125

Thr Ser Arg Phe Gln Ile Leu Glu Gln Asn Trp Asn Gly Trp Ala Asn
    130                 135                 140

Lys Lys Pro Ser Leu Arg Trp Asp Asn Tyr Tyr Gly Leu Thr His Phe
145                 150                 155                 160

Ile Val Pro Pro Val Ala Lys Glu Asn Lys Ala Val Ser Ser Ser Lys
                165                 170                 175
```

Gln Gln Ala Pro Lys Gln Lys Val Lys Lys Ala Ser Thr Lys Lys Ala
            180                 185                 190

Leu Pro Lys Ile Thr Lys His Ile Thr Gly Tyr Asn Met Asp Lys Arg
            195                 200                 205

Gly Tyr Asn Pro Lys Gly Val Val Leu His Asn Asp Ala Gly Gly Met
            210                 215                 220

Asn Tyr Lys Gln Tyr Tyr Asn Asn Leu Val Asn Ala Asn Tyr Asp Arg
225                 230                 235                 240

Leu Ala Arg Gly Ile Ala His Ala Tyr Val Asp Arg Thr Gly Ile Trp
                245                 250                 255

Glu Ala Ile Asp Glu Ser Arg Ile Ala Trp His Val Ala Asp Gly Thr
            260                 265                 270

Arg Pro Gly Ser Gly Asn His Asp Phe Tyr Gly Ile Glu Val Asn Gln
            275                 280                 285

Ser Leu Arg Ala Ser Asp Lys Glu Phe Leu Glu Asn Glu Gln Ala Val
            290                 295                 300

Phe Gln Phe Ala Ala Glu Lys Leu Lys Lys Trp Gly Leu Pro Ala Asn
305                 310                 315                 320

Arg Asn Thr Val Arg Leu His Asn Glu Phe Ser Gln Thr Ser Cys Pro
                325                 330                 335

His Arg Ser Met Val Leu His Thr Gly Leu Asp Pro Leu Tyr His Ser
            340                 345                 350

Ile Thr Glu His Ala Arg Leu Lys Leu Lys Asp Tyr Phe Ile Lys Gln
            355                 360                 365

Ile Arg Ala Tyr Met Asp Gly Lys Lys Pro Thr Ser Lys Val Val Val
            370                 375                 380

Ser Lys Pro Gly Ser Ala Ser Thr Pro Ala Thr Arg Lys Leu Glu His
385                 390                 395                 400

His His His His
            405

<210> SEQ ID NO 17
<211> LENGTH: 1314
<212> TYPE: DNA
<213> ORGANISM: Bacteriophage Phi SH2

<400> SEQUENCE: 17
atgaaaacac aagcagagat taataaacgg ttagacgctt atagaaaagg cacagttgat      60
agtccatata gagttaaagt ttggacgagt tacgataacc gtttctatcc aatggaaccg     120
ggctgtatcg atgtagacaa aagtttccac gctcaatgtg ctgatttaac aatcgactat     180
attttgtggc ttactgataa tgagtttaga attagaggga atgcaaaaga tgcaataaac     240
cctaaaaaga ataagttgcc agaaggatgg aaaattgttt taaacagacc ttcaacagtc     300
cctagaaaag gttggatagc tgtttttact gatggaactt attgggaata cggtcacatt     360
ggtatggttt atgatggtgg taatacaagt cgtttttcaaa ttttagagca aaactgaat     420 ggttgggcta ataagaaacc tagcctacgt tgggataatt attatggttt aactcatttt     480
attgttccac cagtagctaa agaaaataaa gctgtttcat caagcaaaca acaagcacct     540
aaacaaaaag ttaaaaaagc atctactaaa aaagcattac ctaaaatcac taaacacatc     600
actggttata atatggataa acgaggttac aaccctaaag tgtagttttt acacaatgat     660
gcaggaggta tgaactataa acaatattac aacaacttag ttaatgctaa ctatgaccgt     720
ttagcgcgtg gtatcgcaca tgcttatgtt gatagaacag gcatttggga agcaatagac     780

```
gaaagtcgta tagcgtggca tgtagcagat ggcactcgac ctggaagtgg taatcatgat    840
ttctacggta tcgaagtgaa tcaatcatta cgtgcaagtg ataaagaatt cttagagaat    900
gaacaagctg ttttccaatt cgcagcagaa aaactaaaaa agtggggatt accagcaaac    960
agaaataccg ttcgtttgca taatgaattt agtcagacaa gttgtccaca cagaagtatg    1020
gtgcttcata ctggtttaga tccgttgtat cactcaatta ctgaacatgc acgactaaaa    1080
ttaaaagatt acttcattaa acaaattaga gcgtatatgg atggtaagaa accaacttct    1140
aaagtagttg taagcaaacc gggtagtgct tctacaccag ctacacgtaa agacgctaac    1200
ggttatagag aaaatccgca tgggacgtta tataaagaag aacacgcaac atttacagca    1260
aatgctaaca tcatcactcg ttacgttctc gagcaccacc accaccacca ctga          1314
```

<210> SEQ ID NO 18
<211> LENGTH: 437
<212> TYPE: PRT
<213> ORGANISM: Bacteriophage Phi SH2

<400> SEQUENCE: 18

```
Met Lys Thr Gln Ala Glu Ile Asn Lys Arg Leu Asp Ala Tyr Arg Lys
1               5                   10                  15

Gly Thr Val Asp Ser Pro Tyr Arg Val Lys Val Trp Thr Ser Tyr Asp
            20                  25                  30

Asn Arg Phe Tyr Pro Met Glu Pro Gly Cys Ile Asp Val Asp Lys Ser
        35                  40                  45

Phe His Ala Gln Cys Ala Asp Leu Thr Ile Asp Tyr Ile Leu Trp Leu
    50                  55                  60

Thr Asp Asn Glu Phe Arg Ile Arg Gly Asn Ala Lys Asp Ala Ile Asn
65                  70                  75                  80

Pro Lys Lys Asn Lys Leu Pro Glu Gly Trp Lys Ile Val Leu Asn Arg
                85                  90                  95

Pro Ser Thr Val Pro Arg Lys Gly Trp Ile Ala Val Phe Thr Asp Gly
            100                 105                 110

Thr Tyr Trp Glu Tyr Gly His Ile Gly Met Val Tyr Asp Gly Gly Asn
        115                 120                 125

Thr Ser Arg Phe Gln Ile Leu Glu Gln Asn Trp Asn Gly Trp Ala Asn
    130                 135                 140

Lys Lys Pro Ser Leu Arg Trp Asp Asn Tyr Tyr Gly Leu Thr His Phe
145                 150                 155                 160

Ile Val Pro Pro Val Ala Lys Glu Asn Lys Ala Val Ser Ser Ser Lys
                165                 170                 175

Gln Gln Ala Pro Lys Gln Lys Val Lys Lys Ala Ser Thr Lys Lys Ala
            180                 185                 190

Leu Pro Lys Ile Thr Lys His Ile Thr Gly Tyr Asn Met Asp Lys Arg
        195                 200                 205

Gly Tyr Asn Pro Lys Gly Val Val Leu His Asn Asp Ala Gly Gly Met
    210                 215                 220

Asn Tyr Lys Gln Tyr Tyr Asn Asn Leu Val Asn Ala Asn Tyr Asp Arg
225                 230                 235                 240

Leu Ala Arg Gly Ile Ala His Ala Tyr Val Asp Arg Thr Gly Ile Trp
                245                 250                 255

Glu Ala Ile Asp Glu Ser Arg Ile Ala Trp His Val Ala Asp Gly Thr
            260                 265                 270

Arg Pro Gly Ser Gly Asn His Asp Phe Tyr Gly Ile Glu Val Asn Gln
        275                 280                 285
```

```
Ser Leu Arg Ala Ser Asp Lys Glu Phe Leu Glu Asn Glu Gln Ala Val
    290                 295                 300

Phe Gln Phe Ala Ala Glu Lys Leu Lys Lys Trp Gly Leu Pro Ala Asn
305                 310                 315                 320

Arg Asn Thr Val Arg Leu His Asn Glu Phe Ser Gln Thr Ser Cys Pro
                325                 330                 335

His Arg Ser Met Val Leu His Thr Gly Leu Asp Pro Leu Tyr His Ser
            340                 345                 350

Ile Thr Glu His Ala Arg Leu Lys Leu Lys Asp Tyr Phe Ile Lys Gln
        355                 360                 365

Ile Arg Ala Tyr Met Asp Gly Lys Lys Pro Thr Ser Lys Val Val
    370                 375                 380

Ser Lys Pro Gly Ser Ala Ser Thr Pro Ala Thr Arg Lys Asp Ala Asn
385                 390                 395                 400

Gly Tyr Arg Glu Asn Pro His Gly Thr Leu Tyr Lys Glu Glu His Ala
                405                 410                 415

Thr Phe Thr Ala Asn Ala Asn Ile Ile Thr Arg Tyr Val Leu Glu His
            420                 425                 430

His His His His His
        435

<210> SEQ ID NO 19
<211> LENGTH: 690
<212> TYPE: DNA
<213> ORGANISM: Bacteriophage Phi SH2

<400> SEQUENCE: 19
atgcaagcac ctaaacaaaa agttaaaaaa gcatctacta aaaagcatt acctaaaatc        60 actaaacaca tcactggtta taatatggat aaacgaggtt acaaccctaa aggtgtagtt      120
ttacacaatg atgcaggagg tatgaactat aaacaatatt acaacaactt agttaatgct      180
aactatgacc gtttagcgcg tggtatcgca catgcttatg ttgatagaac aggcatttgg      240
gaagcaatag acgaaagtcg tatagcgtgg catgtagcag atggcactcg acctggaagt      300
ggtaatcatg atttctacgg tatcgaagtg aatcaatcat acgtgcaag tgataaagaa      360 ttcttagaga atgaacaagc tgttttccaa ttcgcagcag aaaaactaaa aaagtgggga      420
ttaccagcaa acagaaatac cgttcgtttg cataatgaat ttagtcagac aagttgtcca      480
cacagaagta tggtgcttca tactggttta gatccgttgt atcactcaat tactgaacat      540
gcacgactaa aattaaaaga ttacttcatt aaacaaatta gagcgtatat ggatggtaag      600
aaaccaactt ctaaagtagt tgtaagcaaa ccgggtagtg cttctacacc agctacacgt      660
aaactcgagc accaccacca ccaccactga                                       690

<210> SEQ ID NO 20
<211> LENGTH: 229
<212> TYPE: PRT
<213> ORGANISM: Bacteriophage Phi SH2

<400> SEQUENCE: 20

Met Gln Ala Pro Lys Gln Lys Val Lys Lys Ala Ser Thr Lys Lys Ala
1               5                   10                  15

Leu Pro Lys Ile Thr Lys His Ile Thr Gly Tyr Asn Met Asp Lys Arg
            20                  25                  30

Gly Tyr Asn Pro Lys Gly Val Val Leu His Asn Asp Ala Gly Gly Met
        35                  40                  45
```

Asn Tyr Lys Gln Tyr Tyr Asn Asn Leu Val Asn Ala Asn Tyr Asp Arg
 50                  55                  60

Leu Ala Arg Gly Ile Ala His Ala Tyr Val Asp Arg Thr Gly Ile Trp
 65                  70                  75                  80

Glu Ala Ile Asp Glu Ser Arg Ile Ala Trp His Val Ala Asp Gly Thr
                 85                  90                  95

Arg Pro Gly Ser Gly Asn His Asp Phe Tyr Gly Ile Glu Val Asn Gln
                100                 105                 110

Ser Leu Arg Ala Ser Asp Lys Glu Phe Leu Glu Asn Glu Gln Ala Val
            115                 120                 125

Phe Gln Phe Ala Ala Glu Lys Leu Lys Lys Trp Gly Leu Pro Ala Asn
130                 135                 140

Arg Asn Thr Val Arg Leu His Asn Glu Phe Ser Gln Thr Ser Cys Pro
145                 150                 155                 160

His Arg Ser Met Val Leu His Thr Gly Leu Asp Pro Leu Tyr His Ser
                165                 170                 175

Ile Thr Glu His Ala Arg Leu Lys Leu Lys Asp Tyr Phe Ile Lys Gln
                180                 185                 190

Ile Arg Ala Tyr Met Asp Gly Lys Lys Pro Thr Ser Lys Val Val Val
            195                 200                 205

Ser Lys Pro Gly Ser Ala Ser Thr Pro Ala Thr Arg Lys Leu Glu His
210                 215                 220

His His His His His
225

<210> SEQ ID NO 21
<211> LENGTH: 786
<212> TYPE: DNA
<213> ORGANISM: Bacteriophage Phi SH2

<400> SEQUENCE: 21
atgcaagcac ctaaacaaaa agttaaaaaa gcatctacta aaaaagcatt acctaaaatc      60
actaaacaca tcactggtta taatatggat aaacgaggtt acaaccctaa aggtgtagtt     120
ttacacaatg atgcaggagg tatgaactat aaacaatatt acaacaactt agttaatgct     180
aactatgacc gtttagcgcg tggtatcgca catgcttatg ttgatagaac aggcatttgg     240
gaagcaatag acgaaagtcg tatagcgtgg catgtagcag atggcactcg acctggaagt     300
ggtaatcatg atttctacgg tatcgaagtg aatcaatcat tacgtgcaag tgataaagaa     360
ttcttagaga atgaacaagc tgttttccaa ttcgcagcag aaaaactaaa aaagtgggga     420
ttaccagcaa acagaaatac cgttcgtttg cataatgaat ttagtcagac aagttgtcca     480
cacagaagta tggtgcttca tactggttta gatccgttgt atcactcaat tactgaacat     540
gcacgactaa aattaaaaga ttacttcatt aaacaaatta gagcgtatat ggatggtaag     600
aaaccaactt ctaaagtagt tgtaagcaaa ccgggtagtg cttctacacc agctacacgt     660
aaagacgcta acggttatag agaaaatccg catgggacgt tatataaaga agaacacgca     720
acatttacag caaatgctaa catcatcact cgttacgttc tcgagcacca ccaccaccac     780
cactga                                                              786

<210> SEQ ID NO 22
<211> LENGTH: 261
<212> TYPE: PRT
<213> ORGANISM: Bacteriophage Phi SH2

<400> SEQUENCE: 22

| | | | | | | | | | | | | | | | |
|---|---|---|---|---|---|---|---|---|---|---|---|---|---|---|---|
| Met | Gln | Ala | Pro | Lys | Gln | Lys | Val | Lys | Ala | Ser | Thr | Lys | Ala |
| 1 | | | | 5 | | | | | 10 | | | | | 15 |
| Leu | Pro | Lys | Ile | Thr | Lys | His | Ile | Thr | Gly | Tyr | Asn | Met | Asp | Lys | Arg |
| | | | 20 | | | | | 25 | | | | | 30 |
| Gly | Tyr | Asn | Pro | Lys | Gly | Val | Val | Leu | His | Asn | Asp | Ala | Gly | Gly | Met |
| | | 35 | | | | | 40 | | | | | 45 |
| Asn | Tyr | Lys | Gln | Tyr | Tyr | Asn | Asn | Leu | Val | Asn | Ala | Asn | Tyr | Asp | Arg |
| | 50 | | | | | 55 | | | | | 60 |
| Leu | Ala | Arg | Gly | Ile | Ala | His | Ala | Tyr | Val | Asp | Arg | Thr | Gly | Ile | Trp |
| 65 | | | | | 70 | | | | | 75 | | | | | 80 |
| Glu | Ala | Ile | Asp | Glu | Ser | Arg | Ile | Ala | Trp | His | Val | Ala | Asp | Gly | Thr |
| | | | | 85 | | | | | 90 | | | | | 95 |
| Arg | Pro | Gly | Ser | Gly | Asn | His | Asp | Phe | Tyr | Gly | Ile | Glu | Val | Asn | Gln |
| | | | 100 | | | | | 105 | | | | | 110 |
| Ser | Leu | Arg | Ala | Ser | Asp | Lys | Glu | Phe | Leu | Glu | Asn | Glu | Gln | Ala | Val |
| | | 115 | | | | | 120 | | | | | 125 |
| Phe | Gln | Phe | Ala | Ala | Glu | Lys | Leu | Lys | Lys | Trp | Gly | Leu | Pro | Ala | Asn |
| | 130 | | | | | 135 | | | | | 140 |
| Arg | Asn | Thr | Val | Arg | Leu | His | Asn | Glu | Phe | Ser | Gln | Thr | Ser | Cys | Pro |
| 145 | | | | | 150 | | | | | 155 | | | | | 160 |
| His | Arg | Ser | Met | Val | Leu | His | Thr | Gly | Leu | Asp | Pro | Leu | Tyr | His | Ser |
| | | | | 165 | | | | | 170 | | | | | 175 |
| Ile | Thr | Glu | His | Ala | Arg | Leu | Lys | Leu | Lys | Asp | Tyr | Phe | Ile | Lys | Gln |
| | | | 180 | | | | | 185 | | | | | 190 |
| Ile | Arg | Ala | Tyr | Met | Asp | Gly | Lys | Lys | Pro | Thr | Ser | Lys | Val | Val | Val |
| | | 195 | | | | | 200 | | | | | 205 |
| Ser | Lys | Pro | Gly | Ser | Ala | Ser | Thr | Pro | Ala | Thr | Arg | Lys | Asp | Ala | Asn |
| | 210 | | | | | 215 | | | | | 220 |
| Gly | Tyr | Arg | Glu | Asn | Pro | His | Gly | Thr | Leu | Tyr | Lys | Glu | Glu | His | Ala |
| 225 | | | | | 230 | | | | | 235 | | | | | 240 |
| Thr | Phe | Thr | Ala | Asn | Ala | Asn | Ile | Ile | Thr | Arg | Tyr | Val | Leu | Glu | His |
| | | | | 245 | | | | | 250 | | | | | 255 |
| His | His | His | His | His |
| | | | 260 |

<210> SEQ ID NO 23
<211> LENGTH: 978
<212> TYPE: DNA
<213> ORGANISM: Bacteriophage Phi SH2

<400> SEQUENCE: 23

```
atgcaagcac ctaaacaaaa agttaaaaaa gcatctacta aaaagcatt acctaaaatc      60
actaaacaca tcactggtta taatatggat aaacgaggtt acaaccctaa aggtgtagtt     120
ttacacaatg atgcaggagg tatgaactat aaacaatatt acaacaactt agttaatgct     180
aactatgacc gtttagcgcg tggtatcgca catgcttatg ttgatagaac aggcatttgg     240
gaagcaatag acgaaagtcg tatagcgtgg catgtagcag atggcactcg acctggaagt     300
ggtaatcatg atttctacgg tatcgaagtg aatcaatcat acgtgcaagt gataaagaa      360
ttcttagaga atgaacaagc tgttttccaa ttcgcagcag aaaaactaaa aaagtgggga     420
ttaccagcaa acagaaatac cgttcgtttg cataatgaat ttagtcagac aagttgtcca     480
cacagaagta tggtgcttca tactggttta gatccgttgt atcactcaat tactgaacat     540
```

```
gcacgactaa aattaaaaga ttacttcatt aaacaaatta gagcgtatat ggatggtaag    600
aaaccaactt ctaaagtagt tgtaagcaaa ccgggtagtg cttctacacc agctacacgt    660
aaagacgcta acggttatag agaaaatccg catgggacgt tatataaaga agaacacgca    720
acatttacag caaatgctaa catcatcact cgttacgttg ggcctttcac aaatatgcct    780
caagctggca ttttaaaagc tggtcaaacg attatatatg atgaagtaat gaaacaagac    840
ggttatattt gggtaggtta cactgcatat aatggcaaac gtgtttattt accagttaga    900
aaatggaaca gagaaacaga tagtgtaggt aaattatggg gagtaatcag tctcgagcac    960
caccaccacc accactga                                                   978

<210> SEQ ID NO 24
<211> LENGTH: 325
<212> TYPE: PRT
<213> ORGANISM: Bacteriophage Phi SH2

<400> SEQUENCE: 24
```

Met Gln Ala Pro Lys Gln Lys Val Lys Lys Ala Ser Thr Lys Lys Ala
1               5                   10                  15

Leu Pro Lys Ile Thr Lys His Ile Thr Gly Tyr Asn Met Asp Lys Arg
            20                  25                  30

Gly Tyr Asn Pro Lys Gly Val Val Leu His Asn Asp Ala Gly Gly Met
        35                  40                  45

Asn Tyr Lys Gln Tyr Tyr Asn Asn Leu Val Asn Ala Asn Tyr Asp Arg
    50                  55                  60

Leu Ala Arg Gly Ile Ala His Ala Tyr Val Asp Arg Thr Gly Ile Trp
65                  70                  75                  80

Glu Ala Ile Asp Glu Ser Arg Ile Ala Trp His Val Ala Asp Gly Thr
                85                  90                  95

Arg Pro Gly Ser Gly Asn His Asp Phe Tyr Gly Ile Glu Val Asn Gln
            100                 105                 110

Ser Leu Arg Ala Ser Asp Lys Glu Phe Leu Glu Asn Glu Gln Ala Val
        115                 120                 125

Phe Gln Phe Ala Ala Glu Lys Leu Lys Lys Trp Gly Leu Pro Ala Asn
    130                 135                 140

Arg Asn Thr Val Arg Leu His Asn Glu Phe Ser Gln Thr Ser Cys Pro
145                 150                 155                 160

His Arg Ser Met Val Leu His Thr Gly Leu Asp Pro Leu Tyr His Ser
                165                 170                 175

Ile Thr Glu His Ala Arg Leu Lys Leu Lys Asp Tyr Phe Ile Lys Gln
            180                 185                 190

Ile Arg Ala Tyr Met Asp Gly Lys Lys Pro Thr Ser Lys Val Val Val
        195                 200                 205

Ser Lys Pro Gly Ser Ala Ser Thr Pro Ala Thr Arg Lys Asp Ala Asn
    210                 215                 220

Gly Tyr Arg Glu Asn Pro His Gly Thr Leu Tyr Lys Glu Glu His Ala
225                 230                 235                 240

Thr Phe Thr Ala Asn Ala Asn Ile Ile Thr Arg Tyr Val Gly Pro Phe
                245                 250                 255

Thr Asn Met Pro Gln Ala Gly Ile Leu Lys Ala Gly Gln Thr Ile Ile
            260                 265                 270

Tyr Asp Glu Val Met Lys Gln Asp Gly Tyr Ile Trp Val Gly Tyr Thr
        275                 280                 285

Ala Tyr Asn Gly Lys Arg Val Tyr Leu Pro Val Arg Lys Trp Asn Arg

```
                290                     295                     300
Glu Thr Asp Ser Val Gly Lys Leu Trp Gly Val Ile Ser Leu Glu His
305                     310                     315                     320

His His His His His
                325

<210> SEQ ID NO 25
<211> LENGTH: 1068
<212> TYPE: DNA
<213> ORGANISM: Bacteriophage Phi SH2

<400> SEQUENCE: 25
atgagcctac gttgggataa ttattatggt ttaactcatt ttattgttcc accagtagct      60
aaagaaaata aagctgtttc atcaagcaaa caacaagcac taaacaaaa agttaaaaaa       120
gcatctacta aaaagcatt acctaaaatc actaaacaca tcactggtta taatatggat       180
aaacgaggtt acaaccctaa aggtgtagtt ttacacaatg atgcaggagg tatgaactat      240
aaacaatatt acaacaactt agttaatgct aactatgacc gttagcgcg tggtatcgca       300
catgcttatg ttgatagaac aggcatttgg gaagcaatag acgaaagtcg tatagcgtgg      360
catgtagcag atggcactcg acctggaagt ggtaatcatg atttctacgg tatcgaagtg      420
aatcaatcat tacgtgcaag tgataaagaa ttcttagaga tgaacaagc tgttttccaa       480
ttcgcagcag aaaaactaaa aaagtgggga ttaccagcaa acagaaatac cgttcgtttg      540
cataatgaat ttagtcagac aagttgtcca cacagaagta tggtgcttca tactggttta      600
gatccgttgt atcactcaat tactgaacat gcacgactaa aattaaaaga ttacttcatt      660
aaacaaatta gagcgtatat ggatggtaag aaaccaactt ctaaagtagt tgtaagcaaa      720
ccgggtagtg cttctacacc agctacacgt aaagacgcta acggttatag agaaaatccg      780
catgggacgt tatataaaga agaacacgca acatttacag caaatgctaa catcatcact      840
cgttacgttg ggccttcac aaaatatgcct caagctggca ttttaaaagc tggtcaaacg      900
attatatatg atgaagtaat gaaacaagac ggttatattt gggtaggtta cactgcatat      960
aatggcaaac gtgtttattt accagttaga aaatggaaca gagaaacaga tagtgtaggt     1020
aaattatggg gagtaatcag tctcgagcac caccaccacc accactga                  1068

<210> SEQ ID NO 26
<211> LENGTH: 355
<212> TYPE: PRT
<213> ORGANISM: Bacteriophage Phi SH2

<400> SEQUENCE: 26

Met Ser Leu Arg Trp Asp Asn Tyr Tyr Gly Leu Thr His Phe Ile Val
1               5                   10                  15

Pro Pro Val Ala Lys Glu Asn Lys Ala Val Ser Ser Lys Gln Gln
            20                  25                  30

Ala Pro Lys Gln Lys Val Lys Lys Ala Ser Thr Lys Lys Ala Leu Pro
        35                  40                  45

Lys Ile Thr Lys His Ile Thr Gly Tyr Asn Met Asp Lys Arg Gly Tyr
    50                  55                  60

Asn Pro Lys Gly Val Val Leu His Asn Asp Ala Gly Gly Met Asn Tyr
65                  70                  75                  80

Lys Gln Tyr Tyr Asn Asn Leu Val Asn Ala Asn Tyr Asp Arg Leu Ala
                85                  90                  95

Arg Gly Ile Ala His Ala Tyr Val Asp Arg Thr Gly Ile Trp Glu Ala
```

```
              100                 105                 110
    Ile Asp Glu Ser Arg Ile Ala Trp His Val Ala Asp Gly Thr Arg Pro
        115                 120                 125

Gly Ser Gly Asn His Asp Phe Tyr Gly Ile Glu Val Asn Gln Ser Leu
    130                 135                 140

Arg Ala Ser Asp Lys Glu Phe Leu Glu Asn Glu Gln Ala Val Phe Gln
    145                 150                 155                 160

Phe Ala Ala Glu Lys Leu Lys Lys Trp Gly Leu Pro Ala Asn Arg Asn
                    165                 170                 175

Thr Val Arg Leu His Asn Glu Phe Ser Gln Thr Ser Cys Pro His Arg
                180                 185                 190

Ser Met Val Leu His Thr Gly Leu Asp Pro Leu Tyr His Ser Ile Thr
            195                 200                 205

Glu His Ala Arg Leu Lys Leu Lys Asp Tyr Phe Ile Lys Gln Ile Arg
        210                 215                 220

Ala Tyr Met Asp Gly Lys Lys Pro Thr Ser Lys Val Val Ser Lys
    225                 230                 235                 240

Pro Gly Ser Ala Ser Thr Pro Ala Thr Arg Lys Asp Ala Asn Gly Tyr
                    245                 250                 255

Arg Glu Asn Pro His Gly Thr Leu Tyr Lys Glu His Ala Thr Phe
                260                 265                 270

Thr Ala Asn Ala Asn Ile Ile Thr Arg Tyr Val Gly Pro Phe Thr Asn
            275                 280                 285

Met Pro Gln Ala Gly Ile Leu Lys Ala Gly Gln Thr Ile Ile Tyr Asp
        290                 295                 300

Glu Val Met Lys Gln Asp Gly Tyr Ile Trp Val Gly Tyr Thr Ala Tyr
    305                 310                 315                 320

Asn Gly Lys Arg Val Tyr Leu Pro Val Arg Lys Trp Asn Arg Glu Thr
                    325                 330                 335

Asp Ser Val Gly Lys Leu Trp Gly Val Ile Ser Leu Glu His His
                340                 345                 350

His His His
            355

<210> SEQ ID NO 27
<211> LENGTH: 24
<212> TYPE: DNA
<213> ORGANISM: Bacteriophage Phi SH2

<400> SEQUENCE: 27
cgcgcgcata tgaaaacaca agca                                          24

<210> SEQ ID NO 28
<211> LENGTH: 27
<212> TYPE: DNA
<213> ORGANISM: Bacteriophage Phi SH2

<400> SEQUENCE: 28
caccacctcg agagctactg gtggaac                                       27

<210> SEQ ID NO 29
<211> LENGTH: 24
<212> TYPE: DNA
<213> ORGANISM: Bacteriophage Phi SH2

<400> SEQUENCE: 29
acacctttct cgaggtaacc tcgt                                          24
```

```
<210> SEQ ID NO 30
<211> LENGTH: 24
<212> TYPE: DNA
<213> ORGANISM: Bacteriophage Phi SH2

<400> SEQUENCE: 30
aacataagcc tcgaggatac cacg                                          24

<210> SEQ ID NO 31
<211> LENGTH: 27
<212> TYPE: DNA
<213> ORGANISM: Bacteriophage Phi SH2

<400> SEQUENCE: 31
tcacttgcac gtaactcgag attcact                                       27

<210> SEQ ID NO 32
<211> LENGTH: 26
<212> TYPE: DNA
<213> ORGANISM: Bacteriophage Phi SH2

<400> SEQUENCE: 32
ctctgactcg aggtgcttca tactgg                                        26

<210> SEQ ID NO 33
<211> LENGTH: 24
<212> TYPE: DNA
<213> ORGANISM: Bacteriophage Phi SH2

<400> SEQUENCE: 33
gtggtgctcg agactgatta ctcc                                          24

<210> SEQ ID NO 34
<211> LENGTH: 27
<212> TYPE: DNA
<213> ORGANISM: Bacteriophage Phi SH2

<400> SEQUENCE: 34
gtgcttcata ctctcgagga tccgttg                                       27

<210> SEQ ID NO 35
<211> LENGTH: 27
<212> TYPE: DNA
<213> ORGANISM: Bacteriophage Phi SH2

<400> SEQUENCE: 35
gaccacctcg agtttacgtg tagctgg                                       27

<210> SEQ ID NO 36
<211> LENGTH: 25
<212> TYPE: DNA
<213> ORGANISM: Bacteriophage Phi SH2

<400> SEQUENCE: 36
tatttgtgaa ctcgagaacg taacg                                         25

<210> SEQ ID NO 37
<211> LENGTH: 35
<212> TYPE: DNA
<213> ORGANISM: Bacteriophage Phi SH2

<400> SEQUENCE: 37
```

```
agtatcaaca catatgcaag cacctaaaca aaaag                              35
```

<210> SEQ ID NO 38
<211> LENGTH: 26
<212> TYPE: DNA
<213> ORGANISM: Bacteriophage Phi SH2

<400> SEQUENCE: 38

```
ctaataagca tatgagccta cgttgg                                        26
```